United States Patent [19]
Stella et al.

[11] Patent Number: 5,874,418
[45] Date of Patent: Feb. 23, 1999

[54] SULFOALKYL ETHER CYCLODEXTRIN BASED SOLID PHARMACEUTICAL FORMULATIONS AND THEIR USE

[75] Inventors: Valentino Stella; Roger A. Rajewski, both of Lawrence, Kans.; James W. McGinity, Austin, Tex.

[73] Assignee: Cydex, Inc., Overland Park, Kans.

[21] Appl. No.: 851,006

[22] Filed: May 5, 1997

[51] Int. Cl.⁶ .......................... A61K 31/735; C07H 13/12; C08B 37/16

[52] U.S. Cl. ............................ 514/58; 514/778; 514/964; 514/965; 536/103

[58] Field of Search .............................. 536/103; 514/58, 514/778, 964, 965

[56] References Cited

U.S. PATENT DOCUMENTS

| | | | |
|---|---|---|---|
| 3,426,011 | 2/1969 | Parmerier et al. | 260/209 |
| 3,816,393 | 6/1974 | Hayashi et al. | 260/209 |
| 4,497,803 | 2/1985 | Harada et al. | 514/450 |
| 4,535,152 | 8/1985 | Szejtli et al. | 536/103 |
| 4,555,504 | 11/1985 | Jones | 514/26 |
| 4,582,900 | 4/1986 | Brandt et al. | 536/103 |
| 4,596,795 | 6/1986 | Pitha | 514/58 |
| 4,638,058 | 1/1987 | Brandt et al. | 536/103 |
| 4,727,064 | 2/1988 | Pitha | 514/58 |
| 4,746,734 | 5/1988 | Tsuchiyama et al. | 536/103 |
| 4,764,604 | 8/1988 | Müller | 536/103 |
| 4,774,329 | 9/1988 | Friedman | 536/103 |
| 4,808,232 | 2/1989 | Beesley | 127/46.3 |
| 4,869,904 | 9/1989 | Uekama et al. | 424/400 |
| 5,134,127 | 7/1992 | Stella et al. | 514/58 |

OTHER PUBLICATIONS

*Pharmaceutical Dosage Forms —Tablets,* vol. 1, 2nd Edition, Herbert A. Lieberman, ed., pp. 372–376, 1990.

Okimoto, et al., "The Interaction of Charged and Uncharged Drugs with Neutral (HP–β–CD) and Anionically Charged (SEB7–β–CD) β–Cyclodextrins," *Pharmaceutical Research,* 13(2):256–264, 1996.

Müller, et al., "Cyclodextrin Derivatives for Solubilisation, Stabalisation, and Absorption of Drugs," Proceedings of the Fourth International Symposium on Cyclodextrins, pp. 369–382, 1988.

Pitha, Josef, "Amorphous Water Soluble Derivatives of Cycodextrins: From Test Tube to Patient," Third International on Recent Advances in Drug Delivery Systems, pp. 1–12, 1987.

Brewster, et al., "Improved Delivery Through Biological Membranes XXXI: Solubilization and Stabilization of an Estradiol Chemical Delivery System by Modified β–Cyclodextrins," *J. Pharm. Sci.,* 77(11):981–985, Nov. 1988.

Muranushi, et al., "Studies on Benexate CD: Effect of Inclusion Compound Formation on the Anti–Ulcer Activity of Benexate, the Effective Ingredient in Benexate CD," *Folia Pharmacol. Japan,* 91(6):377–383, 1988.

Torres–Lanbandeira, et al., "Biopharmaceutical Stability of the Glibornuride/β–Cyclodextrin Inclusion Complex After One Year of Storage," *S.T.P. Pharma. Sciences,* 4(3):235–239, 1994.

Peri, et al., "Inclusion Complexes of Tolnaftate with β–Cyclodextrin and Hydroxypropyl β–Ctckidextrub ," *Drug Development and Industrial Pharmacy,* 20(8):1401–1410, 1994.

Otero–Espinar, et al., "Oral Bioavailability of Naproxen–β–Cyclodextrin Inclusion Compound," *Internat. J. of Pharmaceutics,* 75: 37–44, 1991.

Lin, et al., "Solid Particulates of Drug —β–Cyclodextrin Inclusion Complexes Directly Prepared by a Spray–Drying Technique," *Intern. J. of Pharmaceutics,* 56:249–259, 1989.

Esclusa–Diaz, et al., "Preparation and Evaluation ofKetoconazole —β–Cyclodextrin Multicomponent Complexes," *Intern. J. of Pharmaceutics,* 142:183–187, 1996.

*Primary Examiner*—Gary L. Kunz
*Attorney, Agent, or Firm*—Rick Matos; Akin, Gump, Strauss, Hauer & Feld, L.L.P.

[57] ABSTRACT

Sulfoalkyl ether-cyclodextrin (SAE-CD) based pharmaceutical formulations are provided by the present invention. These formulations comprise SAE-CD derivatives and a therapeutic agent, a major portion of which is not complexed to the SAE-CD. The present formulations are advantageously easier to prepare than other SAE-CD based formulations in the art yet provide similar or improved effectiveness. The SAE-CD derivative can be used to modify the bioavailability and/or rate of bioabsorption of therapeutic agents.

20 Claims, 14 Drawing Sheets

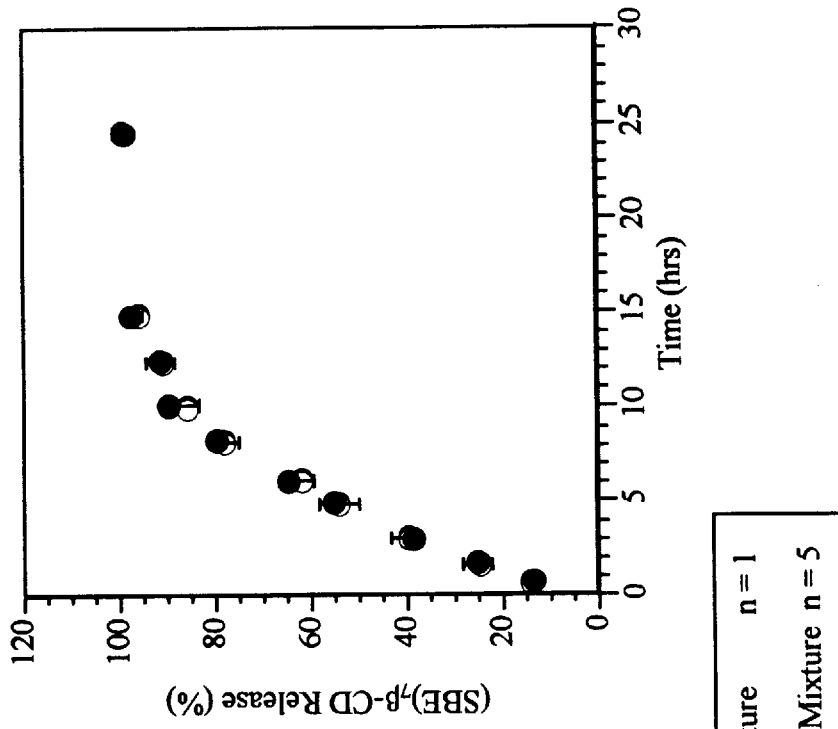
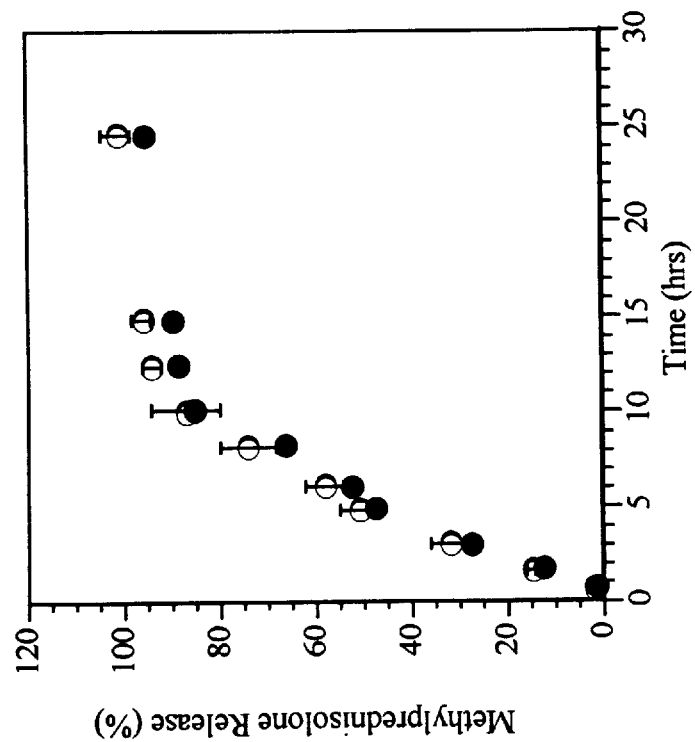
Figure 2a
Figure 2b

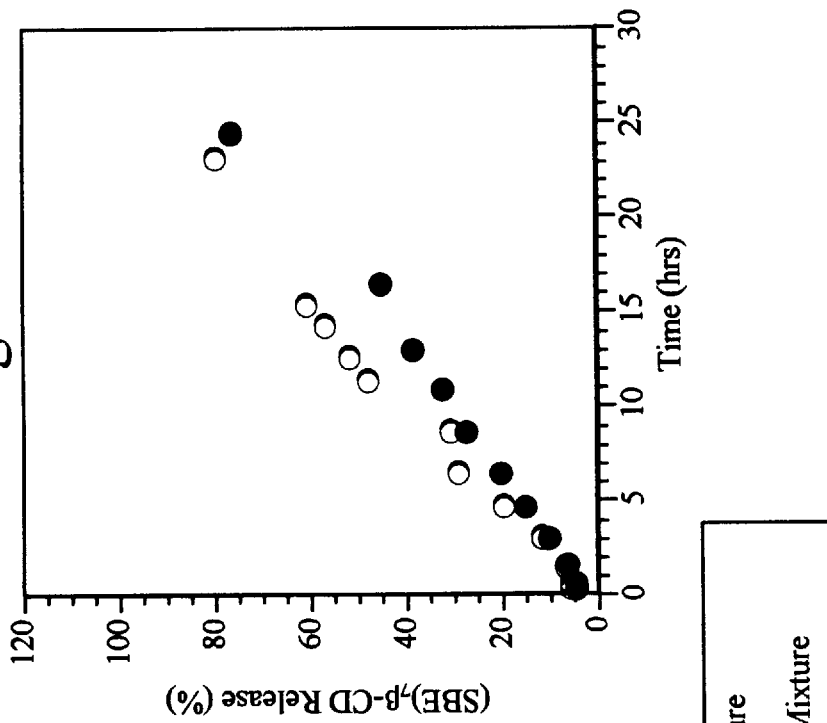
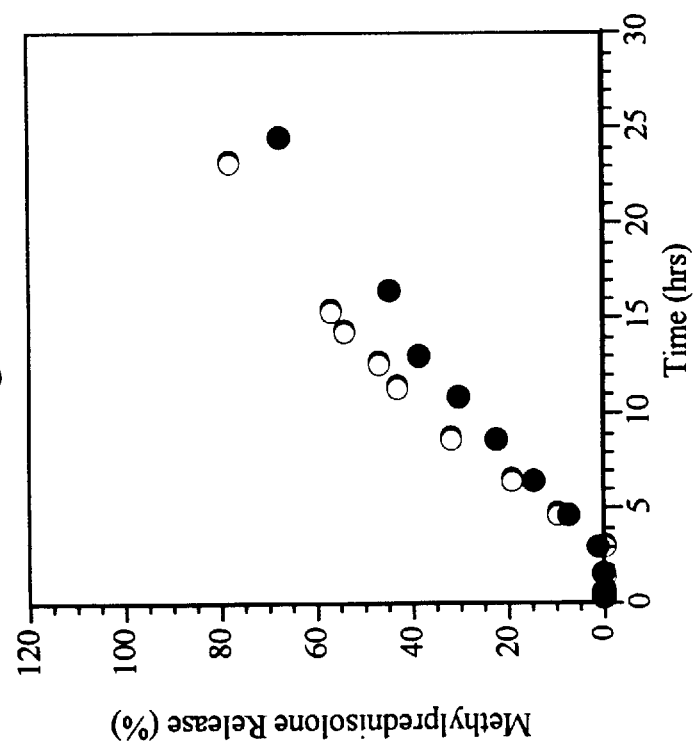
Figure 3a
Figure 3b

SULFOALKYL ETHER CYCLODEXTRIN BASED SOLID PHARMACEUTICAL FORMULATIONS AND THEIR USE

FIELD OF THE INVENTION

This invention relates to cyclodextrin-based solid pharmaceutical formulations. More specifically, it relates to sulfoalkyl ether cyclodextrin (SAE-CD) based formulations wherein a major portion of the therapeutic agent is not complexed with the SAE-CD.

BACKGROUND OF THE INVENTION

U.S. Pat. No. 5,134,127 (the '127 patent) relates to sulfoalkyl ether cyclodextrin (SAE-CD) derivatives. The SAE-CD derivatives are proposed to be used as solubilizing agents for poorly water soluble or water insoluble drugs in various pharmaceutical dosage forms.

Cyclodextrin/drug complexes are typically formed prior to their use in pharmaceutical formulations. The '127 patent relates to compositions and formulations containing a drug complexed to a SAE-CD derivative to form clathrate/drug complexes or inclusion complexes thereof. Pharmaceutical formulations contemplated therein relate to those that include the clathrate complex and a pharmaceutically acceptable carrier.

The SAE-CD/drug clathrate complexes are prepared separately prior to placement in a desired pharmaceutical formulation. Processes to prepare such formulations include steps that require much process monitoring and control and as such may complicate the formulation process. In the pharmaceutical industry, simplified processes are preferred over complex ones, and, with regard to cyclodextrin-containing and, specifically, SAE-CD-containing compositions, a need continues to exist for simplified compositions and processes for their preparation.

Efforts have been made to formulate cyclodextrins with poorly water soluble drugs together as physical mixtures and as inclusion complexes. Muranushi et al. (1988) compared the dissolution profiles for neat benexate, benexate/cyclodextrin physical mixture and benexate-cyclodextrin complex. They reported the significantly increased solubility of benexate when prepared in the complexed vs physyical mixture or neat forms.

Similar results were reported by J. J. Torres-Labandeira et al. (1994) wherein the bioavailability of glibornuride-β-cyclodextrin complex was found to be two to three fold better than that of the glibornuride/β-cyclodextrin physical mixture. D. Peri et al. (1994) also reported that the drug-β-cyclodextrin complex showed improved dissolution over the physical mixture or free drug for tolnaftate. When naproxen and β-cyclodextrin were tested, the respective inclusion complex was found to have a six to nine fold increased solubility at five minutes over that of the physical mixture. (Otero-Espinar et al., 1991)

Further evidence that the drug-β-cyclodextrin inclusion complex possesses a significantly improved dissolution profile than the corresponding physical mixture was reported by Lin et al. (1989) when β-cyclodextrin complexes and physical mixtures of acetaminophen, indomethacin, piroxicam and warfarin were tested. Esclusa-Diaz et al. (1996) also reported that the ketoconazole-β-cyclodextrin complex had a significantly better solubility than the corresponding physical mixture.

U.S. Pat. No. 4,946,686 to McClelland et al. discloses but does not exemplify another application of drug/cyclodextrin physical mixtures. This composition was designed solely for controlled release of a drug wherein solubility modulating units were present as slow release particles dispersed throughout a mixture of drug excipients. All of the components were then surrounded by a microporous water insoluble wall.

Thus, the art generally teaches that a drug-cyclodextrin complex will have significantly better solubility, dissolution profile and bioavailability than its respective physical mixture. A need continues to exist in the pharmaceutical arts for a pharmaceutical formulation containing a drug/cyclodextrin physical mixture that possesses a dissolution profile, bioavailability and solubility approximately those characteristic of the respective drug-cyclodextrin complex.

SUMMARY OF THE INVENTION

As used herein the terms "a" or "an" are taken to mean one or more unless otherwise specified.

The present invention seeks to overcome the disadvantages inherent in known solid pharmaceutical formulations containing a therapeutic agent/cyclodextrin physical mixture. The invention regards simplified sulfoalkyl ether-cyclodextrin-containing solid pharmaceutical compositions and formulations, and methods for their preparation for the delivery of therapeutic agents. The pharmaceutical formulations herein are advantageously prepared by simplified processes not requiring the pre-formation of SAE-CD complexes with the therapeutic agents prior to preparation of the formulations. The formulations comprise a film coating surrounding a solid core which comprises a therapeutic agent/sulfoalkyl ether-cyclodextrin physical mixture that when exposed to water or body fluids forms a therapeutic agent-sulfoalkyl ether-cyclodextrin complex. The therapeutic agent/sulfoalkyl ether-cyclodextrin physical mixture-containing pharmaceutical formulation will possess a solubility, dissolution profile and/or bioavailability which approximates that of the respective inclusion complex.

Accordingly, in one aspect, the present invention provides a solid pharmaceutical formulation comprising a film coating and a solid core, wherein the film coating comprises a film forming agent and a pore forming agent, and the solid core comprises a pharmaceutically acceptable carrier and a physical mixture of a therapeutically effective amount of a therapeutic agent and a sulfoalkyl ether-cyclodextrin (SAE-CD), wherein a major portion of the therapeutic agent is not complexed to the SAE-CD.

The formulations of the present invention are simple compositions made by a simplified process. The present invention also permits the preparation of a wide range of dosage forms having unique characteristics.

In one embodiment, the sulfoalkyl ether-cyclodextrin is a compound of the formula (I):

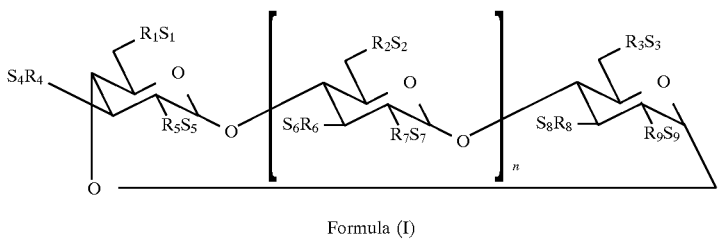

Formula (I)

wherein:

n is 5 or 6;

$R_1$, $R_2$, $R_3$, $R_4$, $R_5$, $R_6$, $R_7$, $R_8$ and $R_9$ are each, independently, —O— or a —O—(C2–C6 alkylene)—$SO_3$— group, wherein at least one of $R_1$ and $R_2$ is independently a —O—(C2–C6 alkylene)—$SO_3$— group, preferably a —O—$(CH_2)_m SO_3$— group, wherein m is 4, (e.g. —$OCH_2CH_2CH_2SO_3$— or —$OCH_2CH_2CH_2CH_2SO_3$—); and $S_1$, $S_2$, $S_3$, $S_4$, $S_5$, $S_6$, $S_7$, $S_8$ and $S_9$ are each, independently, a pharmaceutically acceptable cation which includes, for example, $H^+$, alkali metals (e.g. $Li^+$, $Na^+$, $K^+$), alkaline earth metals (e.g., $Ca^{+2}$, $Mg^{+2}$), ammonium ions and amine cations such as the cations of (C1–C6) alkylamines, piperidine, pyrazine, (C1–C6) alkanolamine and (C4–C8)cycloalkanolamine, wherein a major portion of the therapeutic agent is not complexed with the sulfoalkyl ether-cyclodextrin derivative.

The film coating serves to control the release of the therapeutic agent and the sulfoalkyl ether-cyclodextrin (SAE-CA) from the solid core. The film forming agent is the major component of the film coating and generally serves to slow the release of therapeutic agent and/or SAE-CD. A wide variety of film forming agents are contemplated. The pore forming agent serves to increase the permeability of the film coating by either forming pores or providing regions of enhanced water permeability in the film formed by the film forming agent.

Pharmaceutical formulations described by the invention may further include one or more additional adjuvants and/or active ingredients which can be chosen from those known in the art including flavors, diluents, colors, binders, fillers, surfactants, disintegrants, bioadhesives, penetration enhancers, protease inhibitor stabilizers and compaction vehicles.

In yet another aspect, the present invention is a simplified process for the preparation of sulfoalkyl ether-cyclodextrin derivative-containing solid pharmaceutical formulations. Thus, the invention provides a process for the preparation of a SAE-CD-containing pharmaceutical solid dosage form comprising the steps of:

forming a solid core comprising a physical mixture of a sulfoalkyl ether-cyclodextrin derivative of the formula (I), a pharmaceutical carrier and an effective amount of a therapeutic agent, a major portion of which is not complexed to the sulfoalkyl ether-cyclodextrin derivative; and coating said solid core with a film coating comprising a film forming agent and a pore forming agent to provide a pharmaceutically acceptable solid dosage form.

The process of the present invention does not require that a sulfoalkyl ether-cyclodextrin/therapeutic agent complex be formed. Thus, a major portion the therapeutic agent will remain uncomplexed in the final dosage form.

Yet another aspect of the invention is a method of modifying the bioavailability and/or rate of bioabsorption of therapeutic agents. Thus, in one embodiment, the present invention provides a method of modifying the bioavailability or rate of bioabsorption of a therapeutic agent comprising the steps of:

providing a sulfoalkyl ether-cyclodextrin and a therapeutic agent, a major portion of which is not complexed with the sulfoalkyl ether-cyclodextrin, and administering to a patient the therapeutic agent and sulfoalkyl ether-cyclodextrin, said sulfoalkyl ether-cyclodextrin modifying the bioavailability or rate of bioabsorption of said therapeutic agent.

It is contemplated that the sulfoalkyl ether-cyclodextrin and therapeutic agent will be in the same dosage forms. It is only necessary that the SAE-CD and therapeutic agent become complexed after administration to a patient. A suitable dosage form will permit hydration of the SAE-CD-therapeutic agent physical mixture while in the dosage form to ensure proper formation of the SAE-CD: therapeutic agent complex. A wide range of therapeutic agents, including water soluble, hydrophilic and poorly water soluble, hydrophobic therapeutic agents, can be used in the present formulations.

Other features, advantages and embodiments of the invention will be apparent to those skilled in the art from the following description, examples and appended claims.

BRIEF DESCRIPTION OF THE DRAWINGS

The following drawings form part of the present specification and are included to further illustrate certain aspects of the invention. The invention can be better understood by reference to one or more of the drawings in combination with the detailed description of the specific embodiments presented herein.

FIG. 2a. Release profiles for methyprednisolone and $SBE_7\beta$-CD-containing physical mixture and freeze-dried complex formulations.

FIG. 2b. $SBE_7\beta$-CD-release profile for methyprednisolone physical mixture and freeze-dried complex formulations.

FIGS. 3a and 3b. Methyprednisolone (MP) and $SBE_7\beta$-CD release profiles from physical mixture and freeze-dried complex formulations having a 200μ film coating.

DETAILED DESCRIPTION OF THE INVENTION

Figure 1:
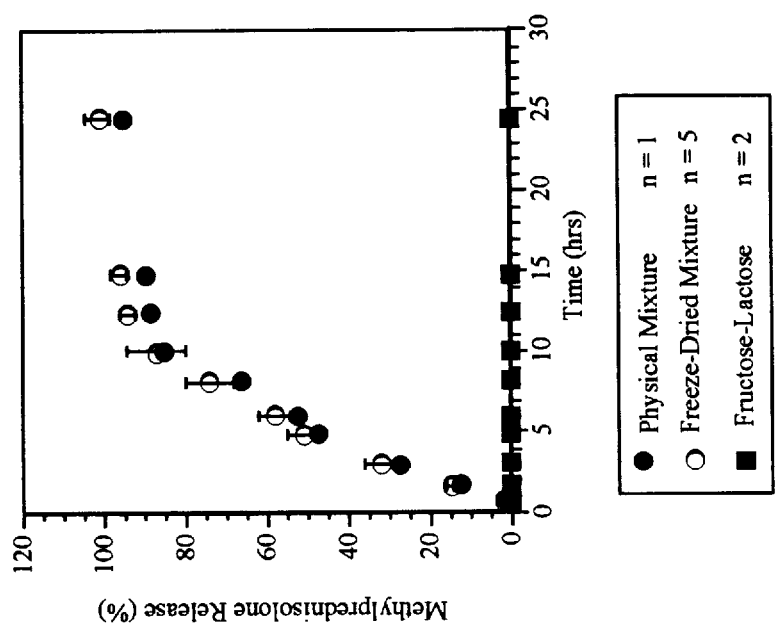
FIG. 1. Release profiles for methyprednisolone and $SBE_7\beta$-CD-containing formulations.

The present invention overcomes the disadvantages inherent in known therapeutic agent/cyclodextrin physical mixture-containing pharmaceutical formulations by providing a formulation that is easy to prepare and has a therapeutic agent solubility, dissolution profile and/or bioavailability that approximates that of its respective therapeutic agent-cyclodextrin complex-containing pharmaceutical formulation. The present invention employs sulfoalkyl ether-cyclodextrins (SAE-CD) derivatives in preparing a wide range of pharmaceutical formulations as herein described. The present formulations can be used for rapid, controlled, delayed, timed, pulsatile and sustained delivery a wide range of therapeutic agents. The formulations can also be included in a wide variety of dosage forms as herein described.

Sulfoalkyl Ether-Cyclodextrin Derivatives

The terms "alkylene" and "alkyl," as used herein (e.g., in the —O—(C2–C6-alkylene)SO$_3$— group or in the alkylamines), include linear, cyclic, and branched, saturated and unsaturated (i.e., containing one double bond) divalent alkylene groups and monovalent alkyl groups, respectively. The term "alkanol" in this text likewise includes both linear, cyclic and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl) cyclic alcohols.

The present invention provides compositions containing a mixture of cyclodextrin derivatives, having the structure set out in formula (I), where the composition overall contains on the average at least 1 and up to 3n+6 alkylsulfonic acid moieties per cyclodextrin molecule. The present invention also provides compositions containing a single type of cyclodextrin derivative, or at least 50% of a single type of cyclodextrin derivative.

The present cyclodextrin derivatives are either substituted at least at one of the primary hydroxyl group (i.e., at least one of R$_1$ to R$_3$ is a substituent), or they are substituted at both the primary hydroxyl group and at the 3-position hydroxyl group (i.e., both at least one of R$_1$ to R$_3$ and at least one of R$_4$, R$_6$ and R$_8$ are a substituent). Substitution at the 2-position hydroxyl group, while theoretically possible, on the basis of the inventors' studies, does not appear to be substantial in the products of the invention.

The cyclodextrin derivatives of the present invention are obtained as purified compositions, i.e., compositions containing at least 95 wt. % of cyclodextrin derivative(s) with the substitution occurring at least on the primary hydroxyl group of the cyclodextrin molecule (i.e. R$_1$, R$_2$ or R$_3$ of formula (I)). In a preferred embodiment, purified compositions containing at least 98 wt. % cyclodextrin derivative(s) can be obtained.

In some of the compositions of the invention unreacted cyclodextrin has been substantially removed, with the remaining impurities (i.e., <5 wt. % of composition) being inconsequential to the performance of the cyclodextrin derivative-containing composition.

The cyclodextrin derivatives used herein can be generally prepared as described in U.S. Pat. No. 5,134,127, which patent is specifically incorporated herein by reference. This preparation process may comprise dissolving the cyclodextrin in aqueous base at an appropriate temperature, e.g., 70° to 80° C., at the highest concentration possible. For example, to prepare the cyclodextrin derivatives herein, an amount of an appropriate alkyl sultone, corresponding to the number of moles of primary CD hydroxyl group present, is added with vigorous stirring to ensure maximal contact of the heterogeneous phase.

The various SAE-CD derivatives evaluated include SBE$_4$β, SBE$_7$β, SBE$_{11}$β and SBE$_4$γ which correspond to SAE-CD derivatives of the formula I wherein n=5, 5, 5 and 6; m is 4; and there are 4, 7, 11 and 4 sulfoalkyl ether substituents present, respectively. It has been found that these SAE-CD derivatives increase the solubility of poorly water soluble drugs to varying degrees. For example, the table below summarizes the binding constant and solubility observed with several SAE-CDs (0.1M at 25° C.) and methylprednisolone.

| SAE-CD type | Binding Constant | Solubility (mg/mL) |
|---|---|---|
| SBE$_4$β | 700 | 5.62 |
| SBE$_7$β | 710 | 5.95 |
| SBE$_{11}$β | 960 | 6.73 |
| SBE$_4$γ | 2600 | 14.74 |

In another embodiment, the present invention employed dipyridamole (DP) which is a basic drug (pka=6.28) having poor aqueous solubility of its free base (3.6 μg/mL at 25° C.) and low and variable bioavailability. SBE$_7$β-CD was found to increase DP solubility dramatically. The table below summarizes the solubility of DP in the presence and absence of SBE$_7$β-CD at different pH values.

| PH | SBE$_7$-β-CD Conc. (M) | DP Solubility (μg/ml) |
|---|---|---|
| 7.0 | 0 | 3.56 |
| 7.0 | 0.1 | 504 |
| 4.0 | 0 | 1990 |
| 4.0 | 0.1 | 16000 |

While the above embodiments exemplify some of the SAE-CD derivatives contemplated by the invention, they should not be considered as limiting the full scope of coverage to which the invention is entitled.

Sulfoalkyl Ether Cyclodextrin-Containing Pharmaceutical Formulation

In order to obtain a cyclodextrin pharmaceutical formulation having acceptable solubility, dissolution profile and bioavailability characteristics, it is generally accepted in the art that a clathrate or an inclusion complex of a cyclodextrin and a therapeutic agent must generally be preformed separately prior to preparation of a pharmaceutical formulation containing the same. However, the present inventors have found that separate preformation of the SAE-CD:therapeutic agent complex is unnecessary.

SAE-CD containing pharmaceutical formulation of the invention will comprise an SAE-CD derivative of the formula (I), as described above, a pharmaceutical carrier, a therapeutic agent and, optionally, additional adjuvants and active ingredients where a major portion of the therapeutic agent is not complexed with the SAE-CD derivative.

Since it is intended that only a major portion of the therapeutic agent included in the present formulation will not be complexed with the SAE-CD, it is possible that some SAE-CD/therapeutic agent complex can be present. The presence of SAE-CD:therapeutic agent complex in the present formulation may or may not be intentional, i.e., the complex can be prepared separately according to the Stella et al. patent and then included in the formulation or the complex may have been formed during the preparation of the present formulation.

By "SAE-CD/therapeutic agent complex" is generally meant a clathrate or inclusion complex of a sulfoalkyl ether-cyclodextrin derivative of the formula (I) and a therapeutic agent. The ratio of SAE-CD:therapeutic agent present in the complex can vary but will generally be in the range of about 1:2 to about 2:1, on a molar basis, respectively, and preferably about 1:1. By "complexed" is meant "being part of a clathrate or inclusion complex with", i.e., a complexed therapeutic agent is part of a clathrate or inclusion complex with a sulfoalkyl ether-cyclodextrin derivative. By "major portion" is meant at least about 50% by weight of the therapeutic compound. Thus, a formulation according to the present invention will contain a therapeutic agent of which more than about 50% by weight is not complexed with an SAE-CD. In various embodiments, preferably greater than 60% by weight, more preferably greater than 75% by weight, even more preferably greater than 90% by weight, and most preferably greater than 95% by weight of the therapeutic agent will remain uncomplexed with an SAE-CD while in the pharmaceutical formulation.

It is intended that the therapeutic agent will begin to complex with the SAE-CD upon administration of a dosage form containing the composition of the invention to a patient and exposure of the composition to body fluids. For example, when a capsule containing powders of therapeutic agent and SAE-CD is administered orally to a patient, the capsule will dissolve, thus permitting gastric juice to contact the therapeutic agent and SAE-CD, and a SAE-CD/therapeutic agent complex will form. A suitable dosage form will permit the physical mixture to become hydrated prior to release from the dosage form to ensure proper complex formation.

The ratio of SAE-CD:therapeutic agent present in the formulation will depend on a number of factors, such as, the intrinsic solubility of the agent, the expected dose of the agent, and the binding constant for inclusion complexation between the specific drug (agent) and the specific SAE-CD. These factors combined will determine the amount of SAE-CD needed in the dosage form and therefore the ratio of SAE-CD:therapeutic agent.

The molecular weight of most SAE-CDs is about 2,000, most therapeutic agents have molecular weights in the range of 200–500, and most drugs form 1:1 inclusion complexes with SAE-CDs. Because of these molecular weight differences, the amount of SAE-CD needed will be minimally 4–10 times the amount of agent. This assumes that one mole of CD will solubilize one mole of drug. However, see below, this assumes an infinitely high binding constant between the agent and the CD. For most solid dosage forms, it is best to have tablets that are less than one gram in total weight and because of the need for other excipients within the tablet formulation, should contain less than 500 mg of CD. Based on this simple assumption, therefore, the amount of drug that can be formulated with the SAE-CD would be less than 50 mg. Since most drugs will not have an infinitely high binding constant with SAE-CDs, the total dose of drug that could be formulated would be <50 mg.

More specifically, agents can form weak through very strong inclusion complexes with SAE-CDs. A very weak inclusion complex would be one where the binding constant is less than about 500 $M^{-1}$; a weak constant would be one where the binding constant is about 500 to about 1000 $M^{-1}$; a moderate binder would have a binding constant of about 1,000 to about 5,000 $M^{-1}$; a strong binder would be one with a binding constant of about 5,000 to about 20,000 $M^{-1}$; and a very strong binder would have a binding constant of greater than about 20,000 $M^{-1}$.

The relative increase in the solubility of a poorly soluble drug in the presence of SAE-CDs is a product of the binding constant and the molar concentration of SAE-CD present. For a very weakly bound drug, a ratio of 100:1, on a molar basis, between SAE-CD and agent might be necessary. If this is the case, the amount of drug in the formulation might have to be as low as 1 mg. If the binding constant between SAE-CD and the agent is very strong, then a ratio of about 1:1 could be permitted. In such a case, a drug dosage as high as 50 mg can be used provided the intrinsic solubility of the drug is suitable. Consider a drug with a binding constant of 10,000 $M^{-1}$, a binding constant that is realistic for a number of drugs. In the presence of 0.1M SAE-CD, the solubility of the drug would be increased about 1,000 fold over the solubility in the absence of the SAE-CD. If the intrinsic solubility of the drug is about 1 ng/ml, then only a solubility of about 1 μg/ml will be possible in the presence of 0.1M SAE-CD, however, if the intrinsic solubility of the drug is about 10 μg/ml, then a solubility of about 10 mg/ml might be possible in the presence of about 0.1N SAE-CD.

For the dosage forms described in this patent, the ratio of SAE-CD:therapeutic agent will generally be in the range of 100:1 to about 1:1 on a molar basis and preferably about 20:1 to about 1:1. Thus, the SAE-CD will generally be present in excess of the therapeutic agent for some agents, while in minimal excess for others. The amount of excess will be determined by the intrinsic solubility of the agent, the expected dose of the agent, and the binding constant for inclusion complexation between the specific drug (agent) and the specific SAE-CD.

Various therapeutic agent/SAE-CD physical mixture-containing pharmaceutical formulations are contemplated by the present invention: osmotic pump tablet, layered tablet, coated tablet, coated pellets, powder for reconstitution, capsules, coated granules and hot-melt extruded films.

The coated tablets, granules and pellets of the invention comprise a film coating and a solid core. The film coating comprises a film coating agent and a pore forming agent. The film coating can comprise plural film forming agents and/or pore forming agents, e.g. combinations of film forming agents can be used in a particular film coating.

The terms "film forming agent" and "release controlling agent" are used interchangeably herein and are intended to include polymeric compounds (of natural, synthetic, semi-synthetic or genetically engineered sources) which will form a film coating around the solid core of the formulation and control the release or slow down the release rate of therapeutic agent or SAE-CD from said core. The film forming agents contemplated by the invention are further descried and, for particular emodiments, exemplified herein.

FIG. 1, which procedure is detailed in Example 1, depicts the release profiles for two methylprednisolone (MP) containing osmotic pump tablets which differ only in the complexation of the SAE-CD and the therapeutic agent. Two compositions, the first containing methylprednisolone/SBE$_7$β-CD physical mixture and the second containing methylprednisolone-SBE$_7$β-CD complex, were formulated into controlled release osmotic pump tablets according to Example 1. The MP and SBE$_7$β-CD (present in a 1:7 molar ratio) along with a pharmaceutical carrier were compressed into a solid core which was spray coated with a mixture of ethylcellulose, PEG3350, PEG400 and ethanol to form a 140 μm thick film coating around the solid core. The dissolution profile was determined using USP dissolution apparatus II (100 rpm, 37° C.) and an HPLC assay for methylprednisolone (MP). A fluorimetric assay employing 2,6-toluidino naphthalene sulfonate (2,6-TNS) was developed for quantitating the SAE-CD. The first formulation, indicated in FIG. 1 by the hollow circles, contains the separately preformed MP-SBE$_7$β-CD freeze-dried complex. The second formulation, indicated by the filled in circles, contains a major portion of uncomplexed MP as a physical mixture with SBE$_7$β-CD. The third formulation, indicate by the squares, contains a physical mixture of lactose, fructose and MP. It is evident by the similarity of the curves corresponding to the preformed complex and the physical mixture, that the latter has a release profile similar to or substantially similar to the former. It should be noted that, for this particular dosage form, the MP and SBE$_7$β-CD had substantially the same release profiles. The results are depicted in FIGS. 2a and 2b for Mp and SBE$_7$β-CD, respectively.

Figure 8:
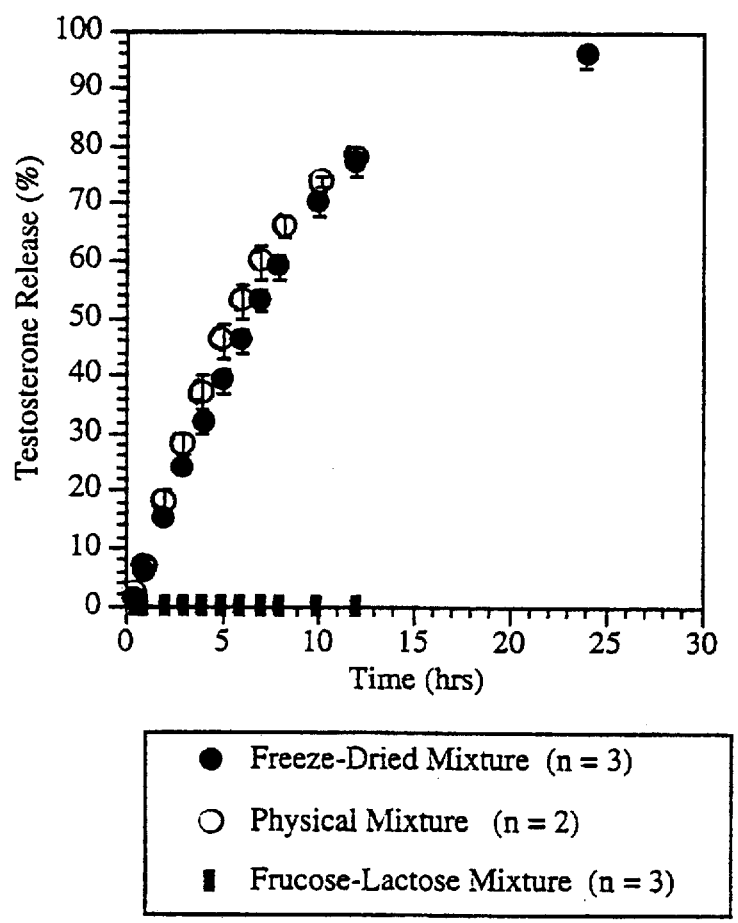
FIG. 8. Release profile for testosterone/SBE$_7$β-CD controlled release tablet formulations.

When the therapeutic agent was testosterone (TST), the physical mixture formulation of SBE$_7$β-CD and TST exhibited the same release profile as the respective freeze dried mixture. (FIG. 8) The solid core of the tablet comprised a 1:1 molar ratio of TST and SBE$_7$β-CD. The film coating of this tablet comprised sorbitol, PEG 400 and cellulose acetate. The release profiles of the physical mixture and complex formulation were compared to that of a baseline TST/fructose-lactose formulation.

Figures 4A, 4B:
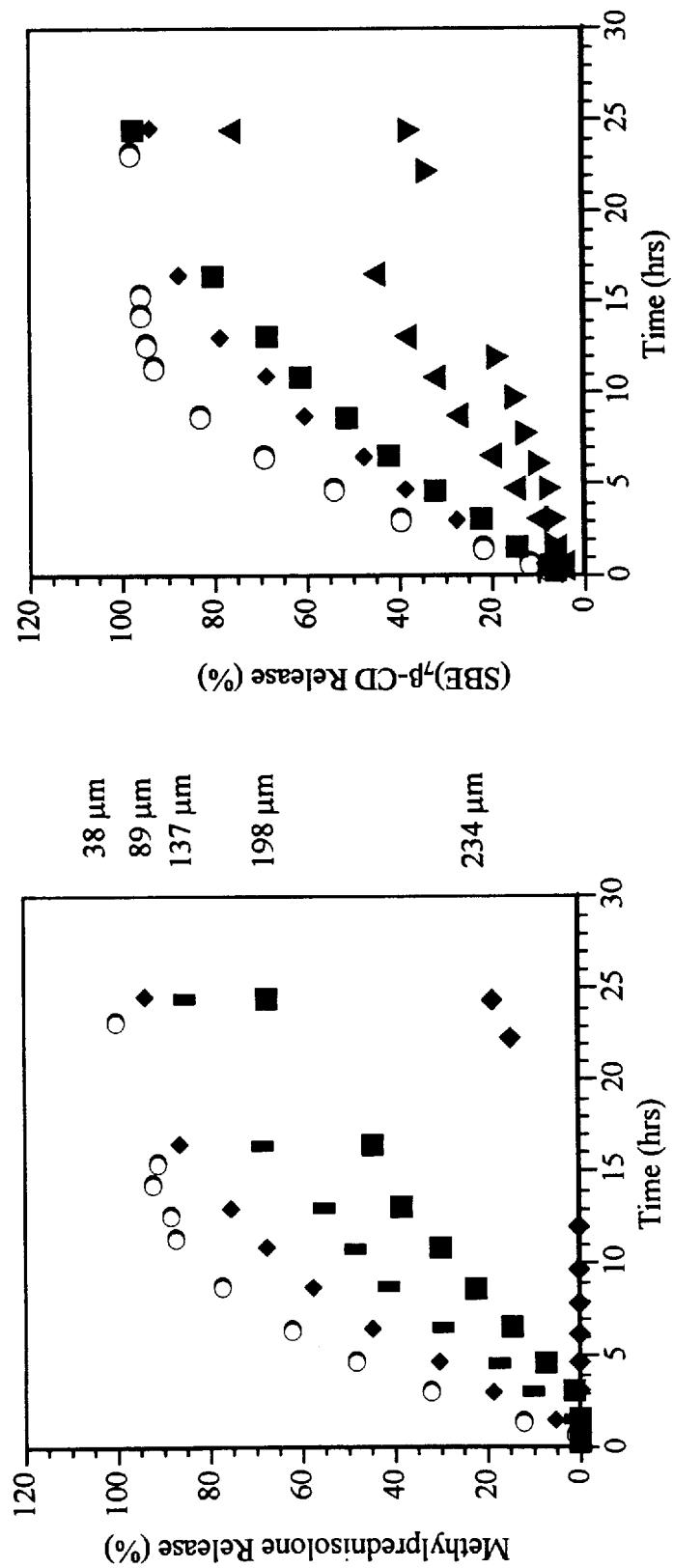
FIGS. 4a and 4b. Effect of film thickness upon MP and $SBE_7\beta$-CD release profiles in a film coated tablet formulation.
Figure 5:
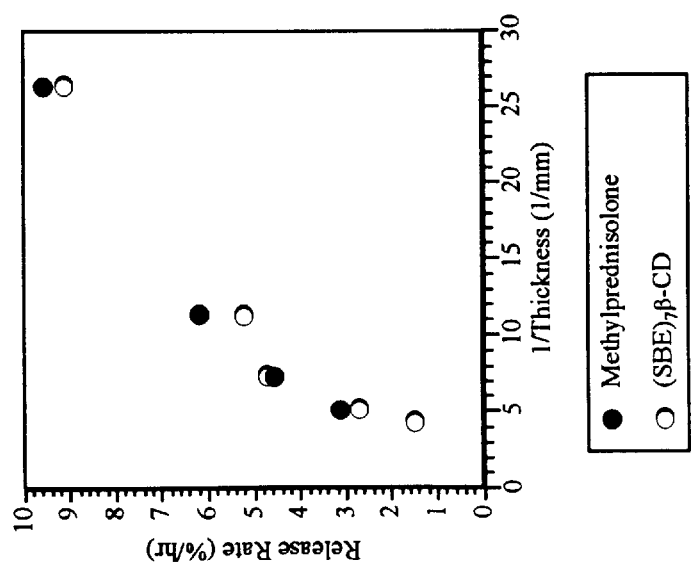
FIG. 5. Relationship between release rate and the inverse of film thickness for MP and $SBE_7\beta$-CD from a physical mixture tablet formulation.
Figure 7B:
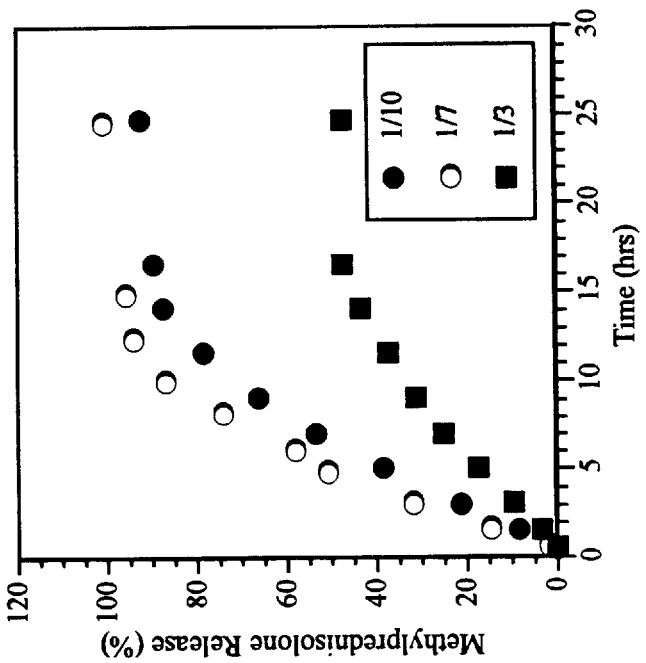
FIGS. 7a and 7b. Impact of the molar ratio of MP/SBE$_7$β-CD upon the MP release from film coated tablet cores comprising a physical mixture or a freeze-dried complex.
Figure 7A:
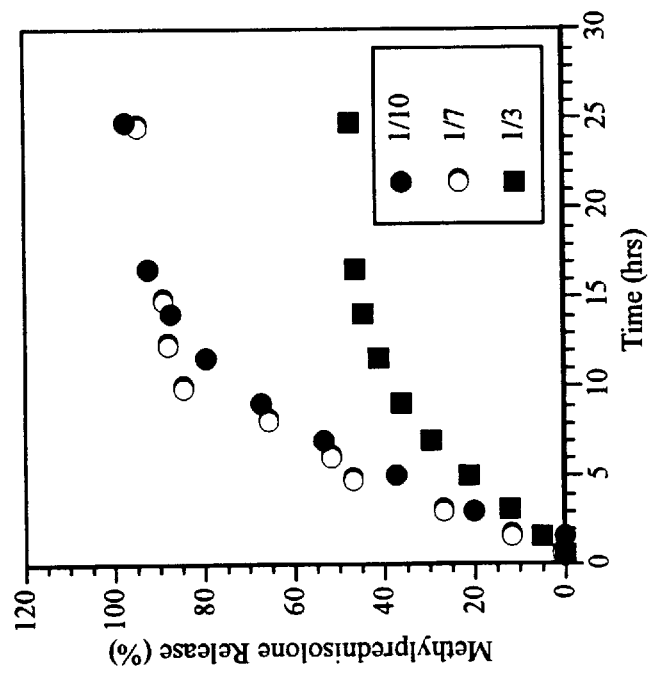
Figure 7D:
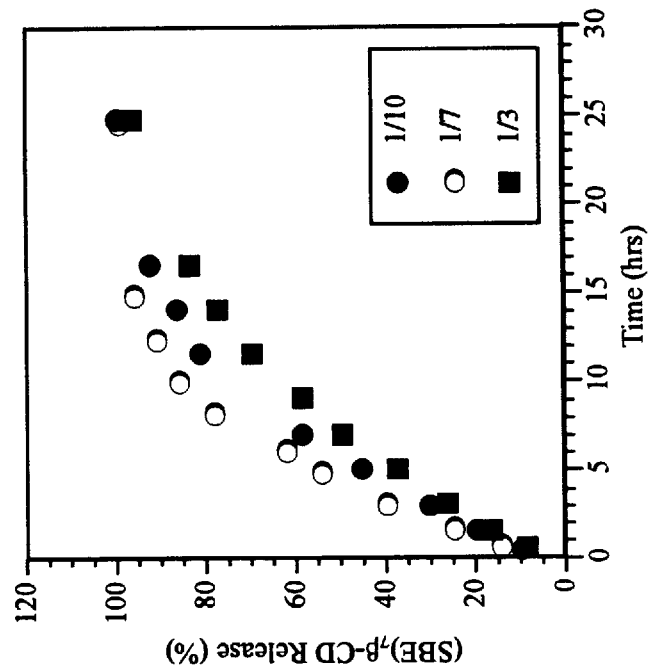
FIGS. 7c and 7d. Effect of MP/SBE$_7$β-CD molar ratio upon the release profile for SBE$_7$β-CD from film coated tablet cores comprising a physical mixture or a freeze-dried complex.
Figure 7C:
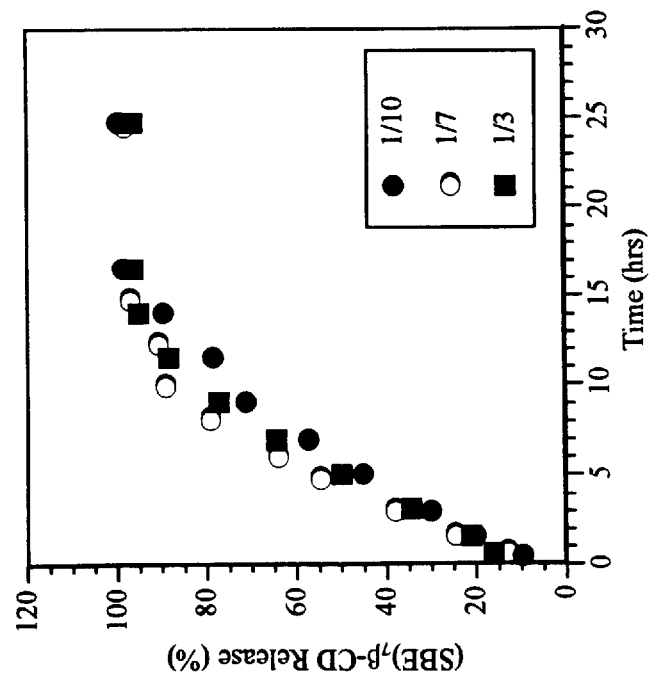

When the thickness of the film coating, or membrane, surrounding the tablet core, which comprised either a physical mixture or a freeze dried complex of MP and SBE$_7$β-CD, was increased to 200 μm, a slight difference was noted in the release profiles of the physical mixture versus the freeze dried complex; however, the SBE$_7$β-CD did have a release profile substantially similar to that of the MP. The results are depicted in FIGS. 3a and 3b for MP and SBE$_7$β-CD, respectively. Additional exemplary film coated tablets having film thicknesses of 38, 89, 137, 198 and 234 μm were prepared and evaluated as above. The results depicted in FIGS. 4a and 4b indicated that SBE$_7$β-CD exhibited substantially the same release profile as MP in each of the dosage forms. In the 234 μm film embodiment, the freeze-dried complex appeared to release SBE$_7$β-CD faster than MP; however, when the release rate data for the physical mixture embodiments of FIGS. 4a and 4b was plotted against the inverse of the film thickness, the results indicated that the SBE$_7$β-CD had a release profile substantially similar to the MP (FIG. 5).

Figure 10:
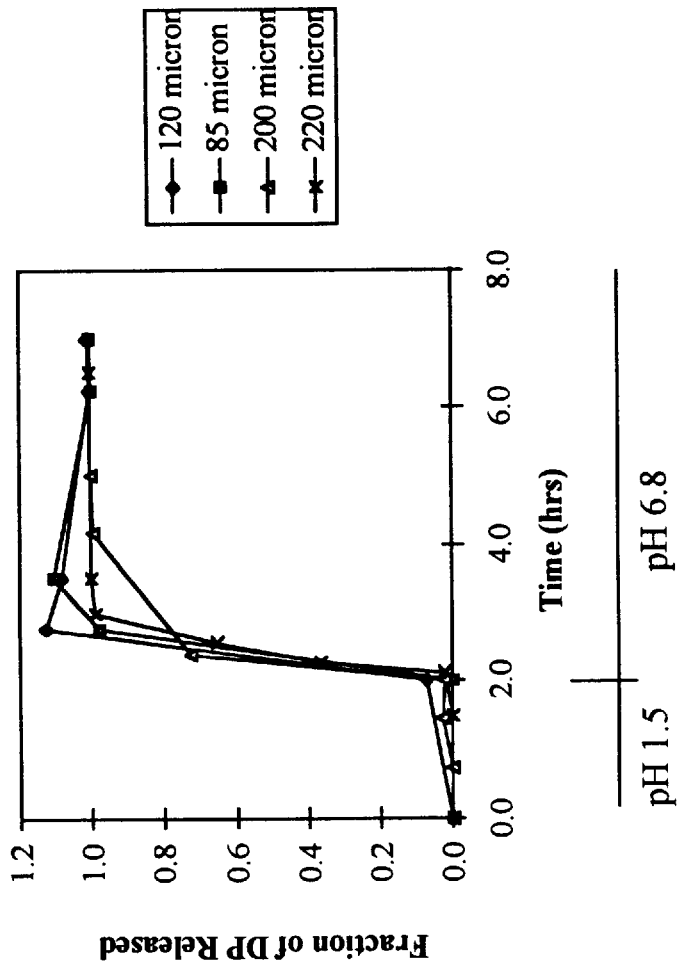
FIG. 10. Effect of film thickness on DP release through EUDRAGIT-L and urea membrane from a tablet core comprising DP and SBE$_7$β-CD physical mixture.

Film thickness need not have a significant impact upon the release profile of a given dosage form. FIG. 10 depicts the effect that film thickness has upon a delayed release formulation comprising an EUDRAGIT-L/urea film coating and a dipyridamole/SBE$_7$β-CD physical mixture solid core. The results indicate that, for this embodiment, the release profile for DP is independent of film thickness but dependent upon solution pH.

Figure 11:
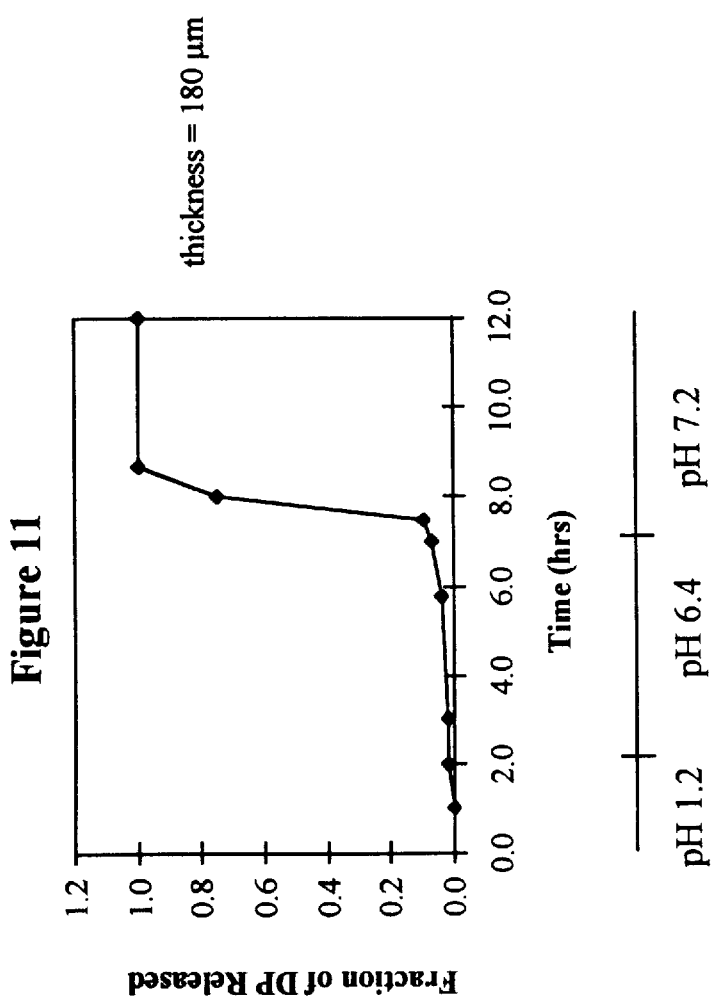
FIG. 11. Release profile for DP through a 180μ thick EUDRAGIT-S and urea film coating surrounding a tablet core comprising a physical mixture of DP and SBE$_7$β-CD.

By changing the film coating composition to EUDRAGIT-S and urea, a delayed release formulation releasing DP at about pH 7.2 rather than at about 6.8 can be made (FIG. 11). The more basic pH corresponds to that found in the lower small intestine or the large intestine of a patient. Accordingly, one can prepare a delayed release formulation for enteric or colorectal release of a therapeutic agent comprising a solid core and a film coating, the solid core comprising a therapeutic agent and an SAE-CD and the film coating comprising a film forming agent which is a polymer with pH dependent solubility.

Figure 6:
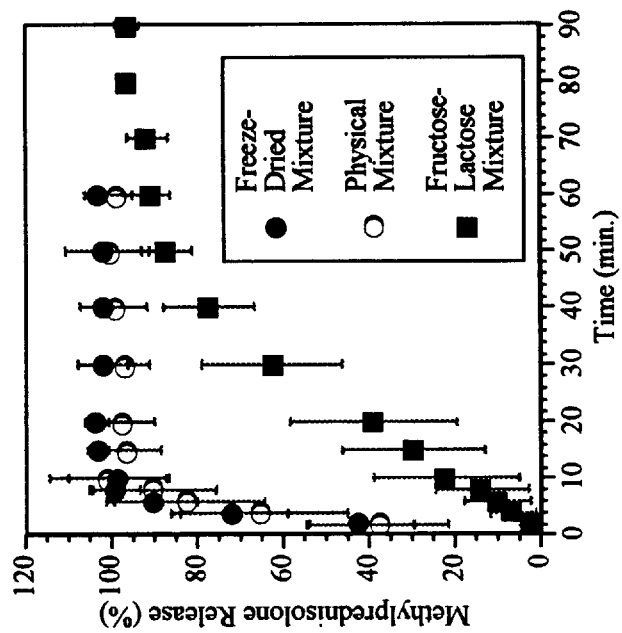
FIG. 6. Effect of $SBE_7\beta$-CD upon the MP release from an uncoated table core comprising either a freeze-dried complex or the physical mixture. A control wherein SBE$_7$β-CD is absent is also depicted.

The film surrounding the solid core will affect the release of MP and SBE$_7$β-CD. In the embodiments of the invention wherein the film surrounding the core is absent, the core comprised of a physical mixture of SBE$_7$β-CD and MP can have the same or substantially the same release characteristics as a core comprised of a complex of the same. FIG. 6 depicts the release profile of MP from solid cores comprising the freeze dried complex (darkened circles), a physical mixture (hollow circles) and a fructose-lactose-MP physical mixture (squares). In this example, the fructose-lactose mixture serves as an osmotic rather than solubilizing agent. The physical mixture exhibits substantially the same release profiles as the complex.

The molar ratio of MP/SBE$_7$β-CD can affect the release profile of a given dosage form. FIGS. 7a–7d depict the release profile of MP and SBE$_7$β-CD from film coated tablets comprising MP and SBE$_7$β-CD as a physical mixture (FIGS. 7a and 7c), and a freeze dried complex (FIG. 7b and 7d), where the MP/SBE$_7$β-CD mole ratios are 1/10, 1/7 and 1/3 (w/w). The results indicate that decreasing the relative amount of SBE$_7$β-CD decreases the observed release profile for MP. Thus, dosage forms having different release profiles can be prepared by controlling the MP/SBE$_7$β-CD ratio. The results also indicate that the physical mixture and the freeze dried complex have substantially the same release characteristics.

Figure 9:
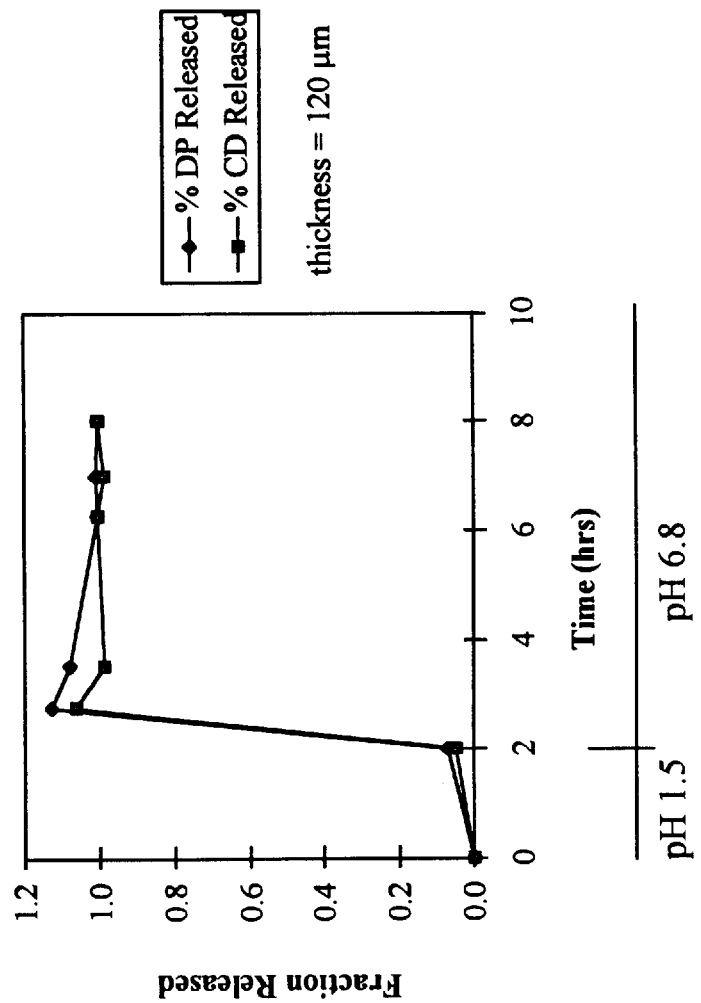
FIG. 9. Release profile for a delayed release formulation of dipyridamole (DP) from an EUDRAGIT-L and urea membrane (120μ thick) coated tablet core comprising a physical mixture of DP and SBE$_7$β-CD.

The film coating employed can comprise a polymer with a pH dependent solubility. FIG. 9 depicts the release profile for a delayed release formulation comprising a tablet core and film coating. The tablet core comprises a physical mixture of SBE$_7$β-CD and dipyridamole (DP). The film coating (150 μm) comprises EUDRAGIT-L which exhibits pH dependent solubility. When the pH of the solution in which the tablet was immersed was raised from 1.5 to 6.8 after two hours, the SBE$_7$β-CD and DP displayed substantially the same release profile. The two hour delay corresponds to a dosage form which would release a major portion of the DP in the ileum or jejunum of a patient.

Figure 12:
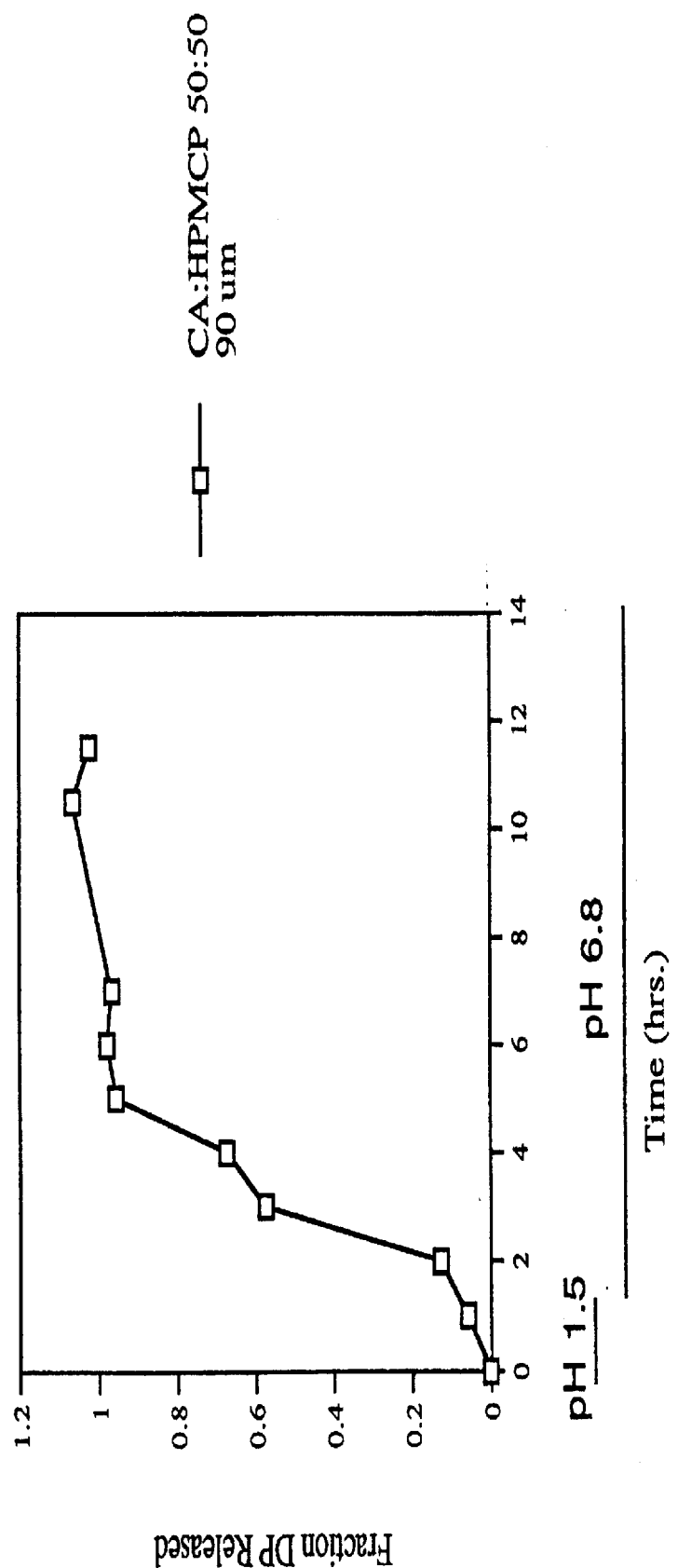
FIG. 12. Release profile for DP from a tablet core comprising a physical mixture of DP and SBE$_7$β-CD coated with a 90μ thick cellulose acetate (CA) and hydroxypropyl methylcellulose phthalate (HPMCP) film.

The film coatings or membranes of the invention can comprise a combination of film forming agents. FIG. 12 depicts one embodiment of the invention wherein the film coating comprises a 1:1 mixture of cellulose acetate (CA) and hydroxypropyl methylcellulose phthalate (HPMCP), and the solid core comprises SBE$_7$β-CD and DP. This combination of film forming agents provides a formulation having a combined delayed and controlled release of therapeutic agent.

Figure 13:
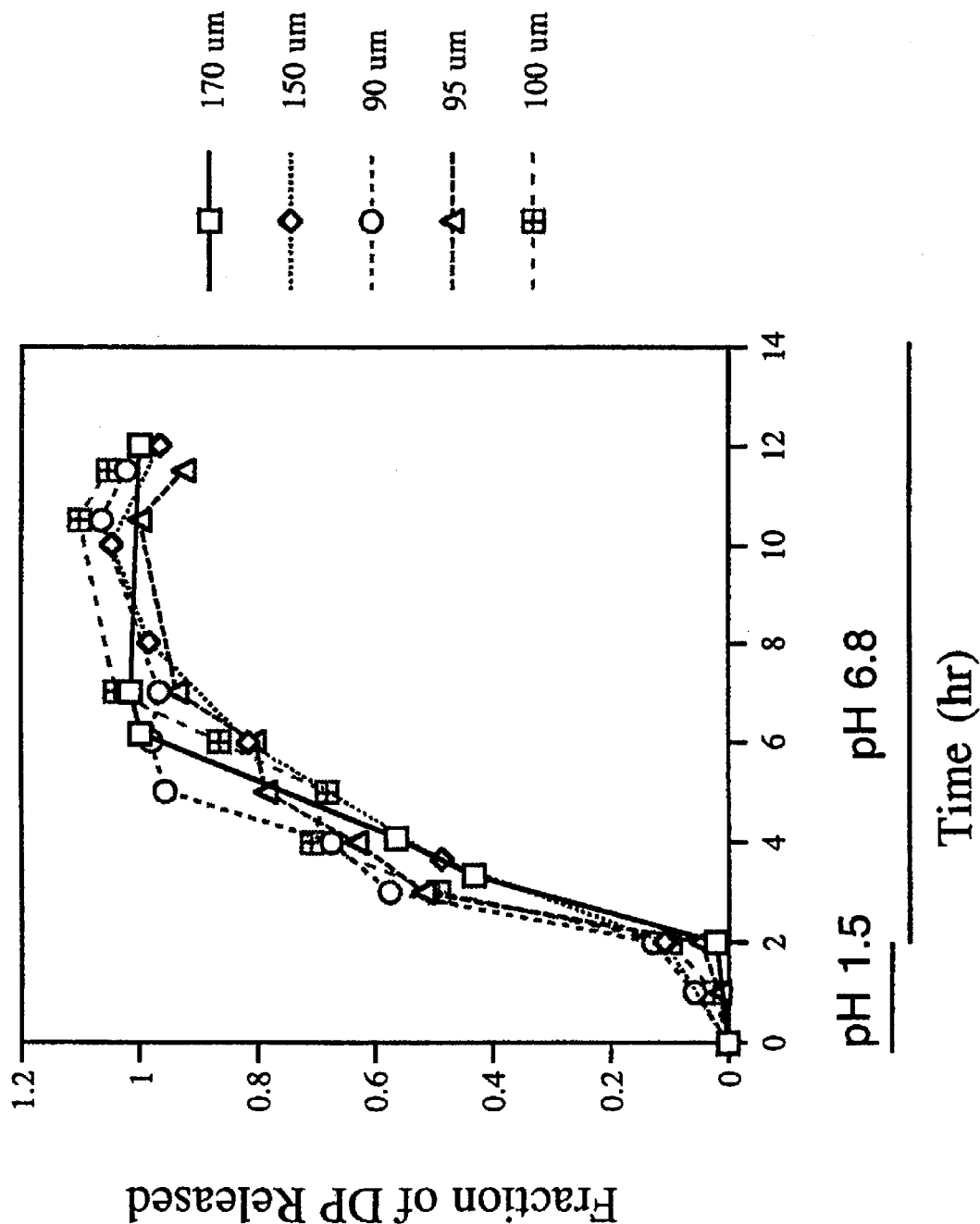
FIG. 13. Impact of film thickness upon DP release from a tablet comprising a physical mixture of DP and SBE$_7$β-CD surrounded by a CA and HPMCP (50:50) film.

Varying the film thickness from 90 μm to 170 μm did not appear to substantially affect the release profile of DP using film forming agents having a pH dependent solubility. Thus, in this embodiment, the invention provides a delayed and controlled release pharmaceutical formulation having a release profile that is only marginally dependent upon film thickness. (FIG. 13)

Figure 14:
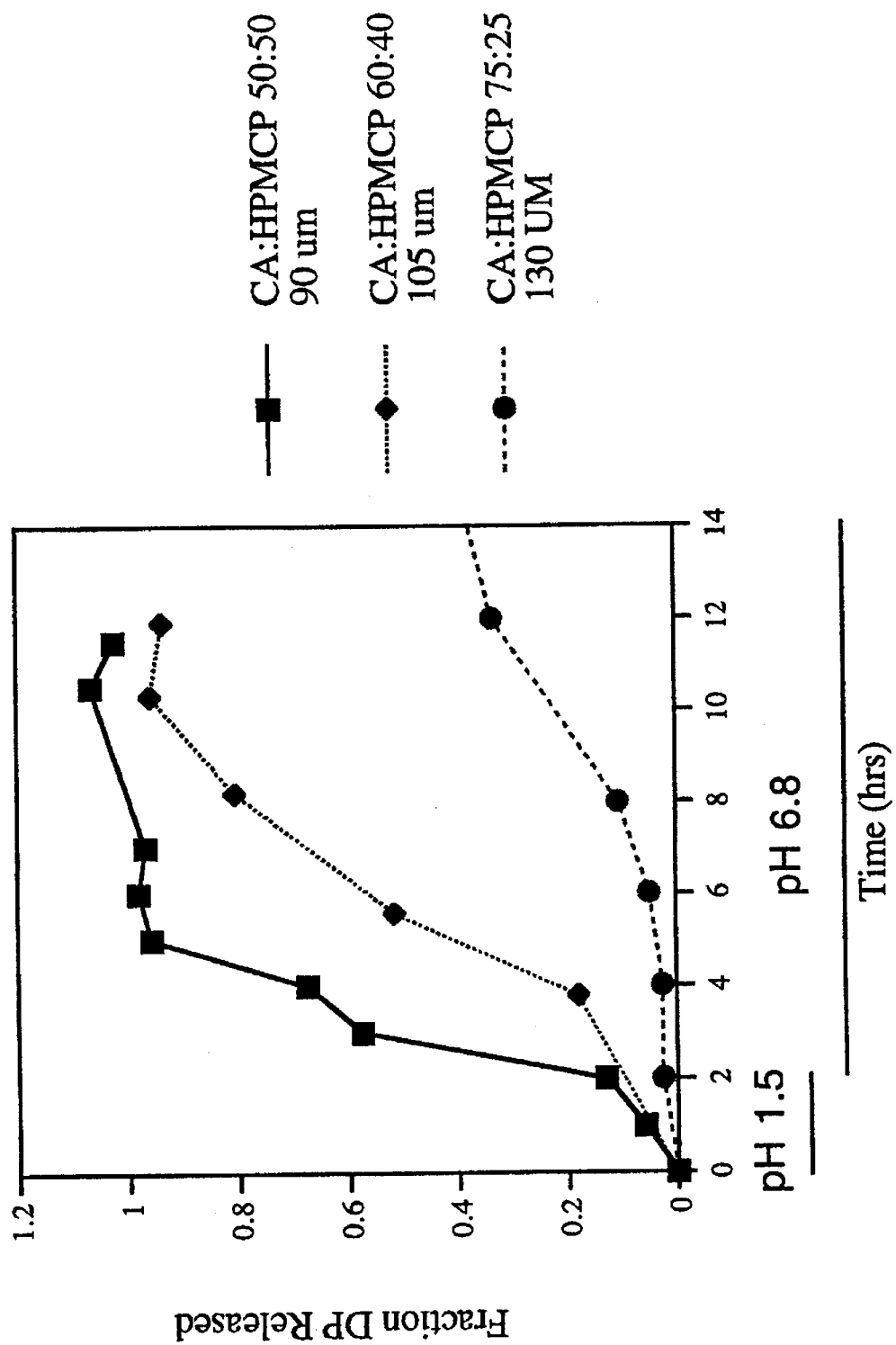
FIG. 14. Release profiles for DP from tablet formulations having a combined delayed and controlled release profile and the effect of film thickness and film composition thereupon.

Particular embodiments of the invention can be made to exhibit delayed release, combined delayed and controlled release and just controlled release. In the embodiment of FIG. 14, a DP/SBE$_7$β-CD containing tablet core was coated with a CA:HPMCP present in a variety of ratios and film thicknesses. The delayed release embodiment, indicated by the squares, comprised a 90 μm film coating which comprised a 1:1 ratio of CA:HPMCP. The combined delayed and controlled release embodiment, indicated by the diamonds, comprised a 105 μm film coating which comprised a 6:4 ratio of CA:HPMCP. Thus, by altering the ratio of CA:HPMCP, one can control the relative contribution of controlled and delayed release to the overall release profile of the dosage form.

It should be noted that in the absence of an SAE-CD according to the present invention, a suitable drug release profile will not be obtained for the therapeutic agents exemplified herein. For example, a tablet core comprising DP, citric acid and fructose-lactose surrounded by a CA:HPMCP (50:50) 120 μm thick film, no release of DP was obtained. In a further example wherein the same tablet core was surrounded by an EUDRAGIT-L and urea (50:50) 120 μm thick film, incomplete release of DP was observed.

Accordingly, the present invention is also a pharmaceutical formulation having a delayed release, controlled release or combined delayed and controlled release profile comprising a tablet core and a film coating around the tablet core, the tablet core comprising a physical mixture of a therapeutic agent and a SAE-CD, and the film coating comprising a combination of film forming agents.

Additional osmotic pump tablets were prepared according to Example 2 and their dissolution characteristics evaluated. These tablets included a DP/SAE-CD-containing tablet core surrounded by film coating comprising one or more of the following: cellulose acetate, ethyl cellulose, wax, EUDRAGIT E100, EUDRAGIT RS, and EUDRAGIT RL, EUDRAGIT L, EUDRAGIT S, cellulose acetate phthalate, hydroxypropyl methylcellulose phthalate and HPMC acetate succinate. The pore forming agent evaluated included poly (ethylene glycol) 3350 (PEG 3350), sorbitol, sucrose and urea.

The term "pore forming agent" as used herein describes an agent that aids in the formation of pores in the film coating of the invention or improves the water permeability of the film. Such pore forming agents can be exemplified with carbohydrates such as lactose, dextrose, fructose, sucrose, mannose; α-hydroxyl acids such as citric acid, tartaric acid, fumaric acid, succinic acid, glycolic acid, lactic acid, combinations thereof and their salts; halide counterions such as bromide, fluoride, iodide and chloride; divalent metal cations such as magnesium and calcium; anionic agents such as phosphates, sulfates, sulfonates, nitrates, bicarbonates, combinations thereof and their salts; cellulosics such as HPC, HPMC, hydroxyethylcellulose, methylcellulose; poly(ethylene oxide); poly(vinyl pyrrolidone); gums and gelling agents such as guar, xanthan gum, alginic acid, acacia, tragacanth, combinations thereof and their salts; clays such as montmorillonite clay, bentonite, Veegum, kaolin clay; miscellaneous ones such as kieselguhr, magnesium silicate, bentone, hectorite, PLURONICS, hydrophilic surfactants; polyols such as sorbitol, mannitol, xylitol; proteins such as albumin, collagen, gelatin; water soluble amino acids; disintegrants such as starch, sodium starch glycolate, croscarmellose; and water soluble organic compounds; and combinations thereof. Pore forming agents which are water permeable can be used to improve the permeability of the film.

The formulations of the invention are intended to form an SAE-CD complex when exposed to bodily fluids. In particular embodiments, the dosage forms of the invention will permit hydration of the SAE-CD/therapeutic agent physical mixture prior to release of the therapeutic agent to aid complex formation.

Method of Modifying Bioavailability and Rate of Bioabsorption

For poorly water soluble, hydrophobic drugs with poor bioavailability, the present invention advantageously provides a method of enhancing water solubility and modifying bioavailability and/or rate of bioabsorption in a patient. For water soluble, hydrophilic drugs with extremely high bioavailability, the present invention provides a method of modifying the rate of bioabsorption in a patient.

By the terms "poorly water soluble" and "hydrophobic" is meant a therapeutic agent having a solubility in neutral water less than about 1 mg/ml at 20° C. By "water soluble" and "hydrophilic" is meant a therapeutic agent having a solubility in neutral water greater than about 1 mg/mL at 20° C.

In some embodiments, the method of the present invention for modifying the bioavailability or rate of absorption of a therapeutic agent comprises the steps of providing a combination of a therapeutic agent and a sulfoalkyl ether-cyclodextrin derivative, and administering the combination to a patient. By "modifying the bioavailability and/or rate of bioabsorption" is meant that the bioavailability and/or rate of bioabsorption of the therapeutic agent when administered in the combination with the SAE-CD will be different than (or modified with respect to) its bioavailability and/or rate of bioabsorption when administered alone.

In other embodiments, the present method comprises the steps of formulating together both the sulfoalkyl ether-cyclodextrin derivative and the uncomplexed therapeutic agent, in a single pharmaceutically acceptable dosage form and administering the dosage form to a patient.

Without being held to the mechanism, it is believed the SAE-CD modifies the bioavailability and/or rate of absorption of the therapeutic agent by forming a clathrate or inclusion complex with it after being exposed to body fluids in a patient. The SAE-CD/therapeutic agent combination can be formulated in a variety of ways as described in detail below. It is only necessary that the SAE-CD be present in an amount sufficient to permit complexation with the therapeutic agent in a patient receiving the formulation.

General

The therapeutic agent which can be included in the present invention can possess a wide range of values for water solubility, bioavailability and hydrophilicity. Thus, the present invention contemplates any therapeutic agent which will form a clathrate or inclusion complex with a SAE-CD derivative of the formula (I). Therapeutic agents to which the present invention is particularly suitable include poorly water soluble, hydrophobic therapeutic agents and water soluble, hydrophilic therapeutic agents. The present invention can be used for formulations in unit doses comprising less than about 500 mg, particularly less than about 150 mg, and more particularly less than about 50 mg of therapeutic agent.

The amount of therapeutic compound incorporated into the present formulations can be selected according to known principles of pharmacy. A therapeutically effective amount of therapeutic compound is specifically contemplated. By the term "therapeutically effective amount," it is understood that, with respect to, for example, pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA.

The therapeutic compound is generally used in finely divided form, i.e. powder or granulate so as to increase the dissolution rate. It is preferable to use a finely powdered therapeutic compound to increase the dissolution rate, more preferably, the therapeutic compound being capable of allowing not less than 80%, desirably not less than 90%, of it to pass through a 100 mesh (150 microns) screen. The amount of therapeutic compound to be incorporated ranges usually from about 0.1 to 50%, preferably about 1 to 25% by weight based on the composition, and the ratio may be suitably modified depending on the therapeutic compound employed.

As the therapeutic agent, use can be made of synthetic antibacterial agents of hardly water-soluble pyridone-carboxylic acid type such as benofloxacin, nalidixic acid, enoxacin, ofloxacin, amifloxacin, flumequine, tosfloxacin, piromidic acid, pipemidic acid, miloxacin, oxolinic acid, cinoxacin, norfloxacin, ciprofloxacin, pefloxacin, lomefloxacin, enrofloxacin, danofloxacin, binfloxacin, sarafloxacin, ibafloxacin, difloxacin and salts thereof. Other therapeutic agents include penicillin, tetracycline, cephalosporins and other antibiotics, antibacterial substances, antihistamines and decongestants, anti-inflammatories, antiparasitics, antivirals, local anesthetics, antifungal, amoebicidal, or trichomonocidal agents, analgesics, antiarthritics, antiasthmatics, anticoagulants, anticonvulsants, antidepressants, antidiabetics, antineoplastics, antipsychotics, antihypertensives and muscle relaxants. Representative antibacterial substances are beta-lactam antibiotics, tetracyclines, chloramphenicol, neomycin, gramicidin, bacitracin, sulfonamides, nitrofurazone, nalidixic acid and analogs and the antimicrobial combination of fludalanine/pentizidone. Representative antihistamines and decongestants are perilamine, chlorpheniramine, tetrahydrozoline and antazoline. Representative anti-inflammatory drugs are cortisone, hydrocortisone, betamethasone, dexamethasone, fluocortolone, prednisolone, triamcinolone, indomethacin, sulindac and its salts and corresponding sulfide. A representative antiparasitic compound is ivermectin.

Representative antiviral compounds are acyclovir and interferon. Representative analgesic drugs are diflunisal, aspirin or acetaminophen. Representative antiarthritics are phenylbutazone, indomethacin, silindac, its salts and corresponding sulfide, dexamethasone, ibuprofen, allopurinol, oxyphenbutazone or probenecid. Representative antiasthma drugs are theophylline, ephedrine, beclomethasone dipropionate and epinephrine. Representative anticoagulants are bishydroxycoumarin, and warfarin. Representative anticonvulsants are diphenylhydantoin and diazepam. Representative antidepressants are amitriptyline, chlordiazepoxide perphenazine, protriptyline, imipramine and doxepin. Representative antidiabetics are insulin, somatostatin and its analogs, tolbutamide, tolazamide, acetohexamide and chlorpropamide. Representative antineoplastics are adriamycin, fluorouracil, methotrexate and asparaginase. Representative antipsychotics are prochlorperazine, thioridazine, molindone, fluphenazine, trifluoperazine, perphenazine, amitriptyline and trifluopromazine. Representative antihypertensives are spironolactone, methyldopa, hydralazine, clonidine, chlorothiazide, deserpidine, timolol, propranolol, metoprolol, prazosin hydrochloride and reserpine. Representative muscle relaxants are succinylcholine-chloride, danbrolene, cyclobenzaprine, methocarbamol and diazepam.

Some other specific examples of therapeutic agents which can be used include, but are not limited to, adiphenine, allobarbital, aminobenzoic acid, amobarbital, ampicillin, anethole, aspirin, azopropazone, azulene barbituric acid, beclomethasone, beclomethasone dipropronate, bencyclane, benzaldehyde, benzocaine, benzodiazepines, benzothiazide, betamethasone, betamethasone 17-valerate, bromobenzoic acid, bromoisovalerylurea, butyl-p-aminobenzoate, chloralhydrate, chlorambucil, chloramphenicol, chlorobenzoic acid, chlorpromazine, cinnamic acid, clofibrate, coenzyme A, cortisone, cortisone acetate, cyclobarbital, cyclohexyl anthranilate, deoxycholic acid, dexamethasone, dexamethasone acetate, diazepam, digitoxin, digoxin, estradiol, flufenamic acid, fluocinolone acetonide, 5-fluorouracil, flurbiprofen, griseofulvin, guaiazulene, hydrocortisone, hydrocortisone acetate, ibuprofen, indican, indomethacin, iodine, ketoprofen, lankacidin-group antibiotics, mefenamic acid, menadione, mephobarbital, metharbital, methicillin, metronidazole, mitomycin, nitrazepam, nitroglycerin, nitrosureas, paramethasone, penicillin, pentobarbital, phenobarbital, phenobarbitone, phenyl-butyric acid, phenyl-valeric acid, phenytoin, prednisolone, prednisolone acetate, progesterone, propylparaben, proscillaridin, prostaglandin A series, prostaglandin B series, prostaglandin E series, prostaglandin F series, quinolone antimicrobials, reserpine, spironolactone, sulfacetamide sodium, sulfonamide, testosterone, thalidomide, thiamine dilaurylsulphate, thiamphenicolpalmitate, thiopental, triamcinolone, vitamin A, vitamin D3, vitamin E, vitamin K3, and warfarin.

The therapeutic compound(s) contained within the pharmaceutical formulation can be formulated as its pharmaceutically acceptable salts. As used herein, "pharmaceutically acceptable salts" refer to derivatives of the disclosed compounds wherein the therapeutic compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent therapeutic compound which contains a basic or acidic moiety by conventional chemical methods. Generally, such salts can be prepared by reacting the free acid or base forms of these compounds with a predetermined amount of the appropriate base or acid in water or in an organic solvent, or in a mixture of the two. Generally, nonaqueous media are preferred. Lists of suitable salts are found in *Remington's Pharmaceutical Sciences,* 18th ed., Mack Publishing Company, Easton, Pa., 1990, chpt. 40, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "active ingredient" is defined as a flavoring agent, a sweetening agent, a vitamin, a mineral and other such compounds for pharmaceutical applications. The present formulation can also contain adjuvants such as coloring agents, disintegrants, lubricants, bioadhesives and the like.

Disintegrants include starches such as corn starch, potato starch, pregelatinized and modified starches thereof, cellulosic agents such as Ac-di-sol, montmorrilonite clays, crosslinked PVP, sweeteners, bentonite and VEEGUM™, microcrystalline cellulose, alginates, sodium starch glycolate, gums such as agar, guar, locust bean, karaya, pecitin and tragacanth. In particular embodiments, a tablet of the invention will not dissolve too rapidly so as to permit hydration the SAE-CD/therapeutic agent physical mixture therein.

Protease inhibitors which can be included in the present formulations include, by way of example and without limitation, antipain, leupeptin, chymostatin, amistatin and puromycin.

Penetration enhancers which can be included in the present formulations include, by way of example and without limitation, calcium chelators such as EDTA and polycarboxylic acids; surfactants such as sodium lauryl sulfate, sodium dodecyl sulfate and tween; bile salts such as sodium taurocholate; fatty acids such as oleic and linoleic acid; and non-surfactants such as AZONE and dialkyl sulfoxides.

Flavors incorporated in the composition may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Particularly preferred flavors are the grape and cherry flavors and citrus flavors such as orange.

Materials to be incorporated in the present formulation can be pretreated to form granules. This process is known as granulation. As commonly defined, "granulation" is any process of size enlargement whereby small particles are gathered together into larger, permanent aggregates to yield a free-flowing composition having a suitable consistency. Such granulated compositions may have consistency similar to that of dry sand. Granulation may be accomplished by agitation in mixing equipment or by compaction, extrusion or agglomeration.

As used in this disclosure, the term "vitamin" refers to trace organic substances that are required in the diet. For the purposes of the present invention, the term "vitamin(s)" include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term "vitamin" are the coenzymes thereof. Coenzymes are specific chemical forms of vitamins. Coenzymes include thiamine pyrophosphates (TPP), flavin mononucleotide (FMM), flavin adenine dinucleotive (FAD), Nicotinamide adenine dinucleotide (NAD), Nicotinamide adenine dinucleotide phosphate (NADP), Coenzyme A (CoA), pyridoxal phosphate, biocytin, tetrahydrofolic acid, coenzyme B12, lipoyllysine, 11-cis-retinal, and 1,25-dihydroxycholecalciferol. The term "vitamin(s)" also includes choline, carnitine, and alpha, beta, and gamma carotenes.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof.

The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

A bioadhesive can also be included in the present formulation. A bioadhesive is defined as a material that adheres to a biological surface such as mucous membrane or skin tissue. A bioadhesive will adherently localize a dosage form onto mucous membrane. The preferred bioadhesive is fibrous or particulate, water swellable but water insoluble. The appropriate ratio of bioadhesive to other components will provide strong bioadhesion. Bioadhesive polymers which can be used in this invention include hydrophilic and water-dispensable polymers, have free carboxylic groups and a relatively high base binding capacity. These polymers as well as hydrophilic cellulosics are polycarboxylated vinyl polymers and polyacrylic acid polymers. Some hydrophilic polysaccharide gums such as guar gum, locust bean gum, psyllium seed gum, and the like are also suitable for use in the formula. The ratio by weight of bioadhesive to active ingredient may be quite broad. In practice, the weight ratio of bioadhesive to active ingredient can be about 1:10 to about 10:1.

The SAE-CD containing pharmaceutical formulation of the invention may require particular hydrophobic or hydrophilic binders in order to obtain suitable product. Suitable hydrophobic binders include cellulose acetate butyrate, cellulose acetate propionate, cellulose propionate high molecular weight (200,000), cellulose propionate medium molecular weight (75,000), cellulose propionate low molecular weight (25,000), cellulose acetate, cellulose nitrate, ethylcellulose, polyvinyl acetate, and the like. Suitable hydrophilic binders include polyvinylpyrrolidone, vinyl alcohol polymer, polyethylene oxide, water soluble or water swellable cellulose and starch derivatives and the like.

Other compounds suitable as film forming agents include cellulose acetate butyrate, cellulose acetate propionate, cellulose propionate, HPMC, carrageenan, cellulose acetate, cellulose nitrate, methylcellulose, hydroxyethylcellulose, ethylcellulose, polyvinyl acetate and latex dispersions, acacia, tragacanth, guar gum, gelatin, and combintions thereof.

Examples of other binders which can be added to the formulation include, for example, acacia, tragacanth, gelatin, starch, cellulose materials such as methyl cellulose and sodium carboxymethyl cellulose, alginic acids and salts thereof, polyethylene glycol, guar gum, polysaccharide, sugars, invert sugars, poloxomers (PLURONIC F68, PLURONIC F127), collagen, albumin, gelatin, cellulosics in nonaqueous solvents, pregelatinized starch, starch paste and combinations of the above and the like. Other binders include, for example, polypropylene glycol, polyoxyethylene-polypropylene copolymer, polyethylene ester, polyethylene sorbitan ester, polyethylene oxide or combinations thereof and the like.

The melting and/or softening point temperatures of these binders usually rise with increase of their molecular weights. Binders having a melting or softening point temperature greater than about 150° C. may require use of a plasticizer during preparation of a suitable dosage form such that the binder melting or softening point temperature will be lowered below 150° C. The binder can be used in any form such as powder, granules, flakes or heat-molten liquid.

As used herein, the term "plasticizer" includes all compounds capable of plasticizing a binder used in the invention. The plasticizer should be able to lower the melting temperature or glass transition temperature (softening point temperature) of the binder. Plasticizers, such as low molecular weight PEG, generally broaden the average molecular weight of the binder thereby lowering its glass transition temperature or softening point. Plasticizers also generally reduce the viscosity of a polymer. It is possible the plasticizer will impart some particularly advantageous physical properties to the formulation of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene glycol), citrate esters, triacetin, propylene glycol phthalate esters, phosphate esters, sebacate esters, glycol derivatives, fatty acid esters, and glycerin.

Such plasticizers can also be ethylene glycol, 1,2-butylene glycol, 2,3-butylene glycol, styrene glycol, diethylene glycol, dipropylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, dimethyldebacate, di-2-ethylhexylsebacate, tricresyl phosphate, triethyl phosphate, triphenyl phosphate, acetylated monoglycerides, mineral oil, castor oil, glyceryl triacetate, butyl stearate, glycerol monostearate, butoxyethyl stearate, stearyl alcohol, cyclohexyl ethyl phthalate, cyclohexyl methyl dibutylphthalate, diethyl phthalate, dibutyl phthalate, diisopropyl phthalate, dimethyl phthalate, dioctyl phthalate, acetyl tributyl citrate, triethyl citrate, acetyl triethyl citrate, tributyl citrate and allyl glycolate. All such plasticizers are commercially available from sources such as Aldrich or Sigma Chemical Co. or Morflex, Inc. It is contemplated and within the scope of the invention, that a combination of plasticizers may be used in the present formulation.

The present pharmaceutical formulations generally comprise a solid core comprising sulfoalkyl ether-cyclodextrin of the formula I, as described above, a pharmaceutically acceptable carrier, and a therapeutically effective amount of a therapeutic agent, a major portion of which is not complexed with the sulfoalkyl ether-cyclodextrin. The solid core will be surrounded by a film coating. These formulations can be included in solid dosage forms such as, by way of example and without limitation, chewable bar, capsule, fiber, film, gel, granule, chewing gum, implant, insert, pellet, powder, tablet, tape, troche, pill, stick, strip and wafer.

Intended routes of administration include oral, peroral, buccal, nasal, implant, rectal, vaginal, sublingual, otic and urethral. The present formulation can be administered with pharmaceutically acceptable carriers or diluents, the proportion and nature of which are determined by the solubility and chemical properties of the therapeutic agent selected, the chosen dosage form, and standard pharmaceutical practice. Solid oral forms may contain conventional excipients, for instance: lactose, sucrose, magnesium stearate, resins and like materials, flavoring, coloring, buffering, preserving, or stabilizing, agents. These formulations can also contain hygroscopic agents which can draw water into a tablet core. Such hygroscopic agents can include: water soluble electrolytes, small organic compounds, osmotic adjusting agents to increase the osmotic pressure within a dosage form and attract water.

As used herein, the term "patient" is taken to mean warm blooded animals such as mammals, for example, cats, dogs, mice, guinea pigs, horses, bovine cows, sheep and humans.

The term "unit dosage form" is used herein to mean a single or multiple dose form containing a quantity of the active ingredient and the diluent or carrier, said quantity being such that one or more predetermined units are normally required for a single therapeutic administration. In the case of multiple dose forms, such as liquids or scored tablets, said predetermined unit will be one fraction such as a half or quarter of a scored tablet of the multiple dose form. It will be understood that the specific dose level for any patient will depend upon a variety of factors including the indication being treated, the therapeutic agent employed, the activity of the therapeutic agent, severity of the indication, patient health, age, sex, weight, diet\and pharmacologic response, the specific dosage form employed and other such factors.

A variety of components or compounds can be used to aid in the preparation of suitable dosage forms for the present invention. Such components or compounds include, without limitation, an acidifying agent, alkalinizing agent, adsorbent, antifungal preservative, antioxidant, buffering agent, colorant, encapsulating agent, flavorant, stiffening agent, suppository base, sweetening agent, tablet antiadherent, tablet binder, tablet and capsule diluent, tablet coating agent, tablet direct compression excipient, tablet disintegrant, tablet glidant, tablet lubricant, tablet/capsule opaquant and tablet polishing agent.

As used herein, the term "acidifying agent" is intended to mean a compound used to provide acidic medium for product stability. Such compounds include, by way of example and without limitation, acetic acid, citric acid, fumaric acid, hydrochloric acid, and nitric acid and the like.

As used herein, the term "alkalinizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium hydroxide, triethanolamine, and trolamine and the like.

As used herein, the term "adsorbent" is intended to mean an agent capable of holding other molecules onto its surface by physical or chemical (chemisorption) means. Such compounds include, by way of example and without limitation, powdered and activated charcoal and the like.

As used herein, the term "preservative" is intended to mean a compound used to prevent the growth of microorganisms. Such compounds include, by way of example and without limitation, benzalkonium chloride, benzethonium chloride, benzyl alcohol, cetylpyridinium chloride, chlorobutanol, phenol, phenylethyl alcohol, phenylmercuric nitrate and thimerosal and the like.

As used herein, the term "antioxidant" is intended to mean an agent which inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and the like.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and the like.

As used herein, the term "colorant" is intended to mean a compound used to impart color to solid (e.g., tablets and capsules) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red and the like. Coloring agents can also include titanium dioxide, natural coloring agents such as grape skin extract, beet red powder, beta-carotene, annato, carmine, turmeric, paprika and the like.

As used herein, the term "encapsulating agent" is intended to mean a compound used to form thin shells for the purpose of enclosing a drug substance or drug formulation for ease of administration. Such compounds include, by way of example and without limitation, gelatin, nylon, biodegradable polyesters, D,L-poly(lactic acid), polylactide-co-glycolic acid, cellulose acetate phthalate and the like.

As used herein, the term "flavorant" is intended to mean a compound used to impart a pleasant flavor and often odor to a pharmaceutical preparation. In addition to the natural flavorants, many synthetic flavorants are also used. Such compounds include, by way of example and without limitation, anise oil, cinnamon oil, cocoa, menthol, orange oil, peppermint oil and vanillin and the like.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and the like.

As used herein, the term "tablet antiadherents" is intended to mean agents which prevent the sticking of table formulation ingredients to punches and dies in a tableting machine during production. Such compounds include, by way of example and without limitation, magnesium stearate, corn starch, silicone dioxide, talc and the like.

As used herein, the term "tablet binders" is intended to mean substances used to cause adhesion of powder particles in table granulations. Such compounds include, by way of example and without limitation, acacia, alginic acid, carboxymethylcellulose sodium, compressible sugar (e.g., NuTab), ethylcellulose, gelatin, liquid glucose, methylcellulose, povidone and pregelatinized starch and the like.

As used herein, the term "tablet and capsule diluent" is intended to mean inert substances used as fillers to create the desired bulk, flow properties, and compression characteristics in the preparation of tablets and capsules. Such compounds include, by way of example and without limitation, dibasic calcium phosphate, kaolin clay, fructose, sucrose, dextrose, lactose, mannitol, microcrystalline cellulose, powdered cellulose, precipitated calcium carbonate, sorbitol, calcium sulfate, starch and the like.

As used herein, the term "tablet coating agent" is intended to mean a compound used to coat a formed tablet for the purpose of protecting against drug decomposition by atmospheric oxygen or humidity, to provide a desired release pattern for the drug substance after administration, to mask the taste or odor of the drug substance, or for aesthetic purposes. The coating may be of various types, including sugar coating, film coating, or enteric coating. Sugar coating is water-based and results in a thickened covering around a formed tablet. Sugar-coated tablets generally dissolve at the higher pH values of the intestines. A film coat is a thin cover around a formed tablet or bead. Unless it is an enteric coat, the film coat will dissolve in the stomach. An enteric-coated tablet or bead will pass through the stomach and break up in the intestines. Some coatings that are water-insoluble (e.g., ethylcellulose) may be used to coat tablets and beads to slow the release of drug as the tablet passes through the gastrointestinal tract. Such compounds for coatings include, by way of example and without limitation, liquid glucose and sucrose are examples of sugar coating agents; hydroxyethyl cellulose, hydroxypropyl cellulose, hydroxypropyl methylcellulose, methylcellulose (e.g., Methocel) and ethylcellulose (e.g., Ethocel) are examples of film coating; and cellulose acetate phthalate and shellac (35% in alcohol, "pharmaceutical glaze") are examples of enteric coating and the like.

As used herein, the term "tablet direct compression excipient" is intended to mean a compound used in direct compression tablet formulations. Such compounds include, by way of example and without limitation, dibasic calcium phosphate (e.g., Ditab), microcrystalline cellulose, Avicel, dextran (EMDEX), sucrose (NUTAB) and the like.

As used herein, the term "tablet glidant" is intended to mean agents used in tablet and capsule formulations to reduce friction during tablet compression. Such compounds include, by way of example and without limitation, colloidal or fumed silica, magnesium stearate, cornstarch, and talc and the like.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, hydrogenated vegetable oil, benzoic acid, poly(ethylene glycol), NaCl, PRUV, zinc stearate and the like.

As used herein, the term "tablet/capsule opaquant" is intended to mean a compound used to render a capsule or a tablet coating opaque. May be used alone or in combination with a colorant. Such compounds include, by way of example and without limitation, titanium dioxide and the like.

As used herein, the term "tablet polishing agent" is intended to mean a compound used to impart an attractive sheen to coated tablets. Such compounds include, by way of example and without limitation, carnauba wax, and white wax and the like.

The present formulation including therapeutic agent/SAE-CD physical mixtures have been found to be particularly suitable for therapeutic agents including simvastatin, cryptophycin, jaspamide, ambrosin, busulfan, propanolol, etoposide, taxol, brefeldin A, Brefeldin A prodrug (NSC#D656202), 9-Amino-20(S)-camptothecin, camptothecin, prednisolone acetate, prednisolone, pancreastatin, rhizoxin, bryostatin 1, taxotere $O_6$-benzylguanine, androstane, guanine, chloramphenicol, dapsone, sulfacone, benclomethasone dipropionate, menadione, tamoxifen citrate, cholesterol, estrone, verapmil HCI, equilin, warfarin, indomethacin, phenytoin, cinnarizine, amiodarone HCI, naproxen, piroxicam, thiabendazole, papaverine, miconazole (free base), nifedipine, testosterone, progesterone, carbamazepine, methylprednisolone, dexamethasone, hydrocortisone and miconazole nitrate.

The foregoing will be better understood with reference to the following examples which detail certain procedures for the preparation of formulations according to the present invention. All references made to these examples are for the purposes of illustration. They are not to be considered limiting as to the scope and nature of the present invention.

EXAMPLE 1

Testosterone—$(SBE)_7$-$\beta$-CD

Sustained Release Formulation

The present example demonstrates the utility of the present invention for the preparation of sustained release formulations with pharmacologically active agent, testosterone providing an example of one such agent.

Phase Solubility Studies

Excess amounts of testosterone were added to 0.25 ml of $(SBE)_7$-$\beta$-CD solutions ranging from 0.0 to 0.05 mol/l. The dispersions were allowed to equilibrate for a minimum of 24 hours in a shaking waterbath (100 spm, 25° C.). The dispersions were centrifuged 10 min. at 2500 rpm, 20 $\mu$l of the supernatant were sampled with a gas-tight 100 $\mu$l syringe (Hamilton Co., NV), diluted with mobile phase and analysed by HPLC for the testosterone concentration in solution. The testosterone-$(SBE)_7$-$\beta$-CD binding constant $K_{1:1}$ was then determined by the method of Higuchi and Connors for an Type $A_L$ diagram.

Tablet Core Preparation

The tablet core was prepared with a 1/1 molar ratio of testosterone/$(SBE)_7$-$\beta$-CD. The tablet core consisted of either the testosterone-$(SBE)_7$-$\beta$-CD complex or the physical mixture of the two compounds. The complex was prepared by freeze-drying a testosterone-$(SBE)_7$-$\beta$-CD solution (5–15% in $(SBE)_{7m}$-$\beta$-CD). Non $(SBE)_7$-$\beta$-CD containing tablets were also prepared. They consisted of a 1/1 ratio of testosterone to a 50:50 (w/w) mixture of fructose and lactose (Fischer Scientific, NJ). The mixtures were ground in a mortar and sieved through a 200 mesh (75 $\mu$m) screen under low humidity conditions. The mixtures were stored in a dessicator when not used. Tablets of around 120 mg were compressed into the dissolution die using a Carver Laboratory Press (Fred S. Carver Inc., NJ) at 1 ton during 1 min.

Semi-permeable membrane preparation

The coating formulation was prepared by dissolving 1.0% of sorbitol (Sigma, MO) in 3.7% of double distilled water and 0.4% of PEG 400 (Sigma, MO). 2.0% of cellulose acetate (CA-398-10, Eastman Chemical Co., TN) were suspended in the solution; 55.7.% of methylene chloride and 37.2% of methanol were added to the mixture. The dispersion was shaken and sonicated until complete dissolution of the solid components. The coating solution was air sprayed (Airbrush, Paasche) on a stainless steel surface under constant air flow (40° C.). They were then left at room temperature during 24 hours. The membranes were peeled off the surface, checked for cracks and flaws under a light microscope (×70) and their thickness was measured using a Micrometer (Ames, MA). The membranes were then secured on the dissolution die containing the tablet, with the face which was sprayed on the steel in contact with the tablet surface.

In vitro Release Studies

The release studies were realized by placing the dissolution die in a USP dissolution apparatus II (Vanderkamp 600, VanKel Industries Inc.) containing 900 ml of water at 37° C., 100 rpm. Samples were collected at various time points. The 100% release was determined by removing the membrane from the die and allowing the drug dissolution to be complete. The samples were analysed by HPLC for testosterone concentration.

Testosterone HPLC detection

Testosterone was detected using a 15 cm ODS Hypersil column followed by UV detection at 238 nm (Shimadzu scientific Instruments, Inc., Japan). The mobile phase was composed of 60% acetonitrile and 40% double distilled water.

EXAMPLE 2

Dipyridamole—$(SBE)_7$-$\beta$-CD

Delayed Release Formulation

Analytical Procedures

Dipyridamole was analyzed using a 15 cm ODS Hypersil column. The sample volume was 20 $\mu$l and the UV detection wavelength was 285 nm (Shimadzu 6A, Shimadzu, Japan). A mobile phase consisting of 70% methanol and 30% ammonium phosphate buffer (pH 5.0) was passed through the column at a flow rate of 1.5 ml/min. $(SBE)_{7m}$-$\beta$-CD was detected by using a fluorimetric assay. 0.2 ml of a 1 mM solution of 2,6-toluidino-naphthalene-sulfonate to 0.8 ml of the sample. This solution was then excited at 325 nm and the emitted fluorescence detected at 455 nm using a Perkin-Elmer (Perkin-Elmer, CT) Fluorescence detector.

Phase Solubility Experiments $(SBE)_7$-β-CD (0–0.1M) solutions were made in different buffer solutions at pH values ranging from 4.0 to 7.0 (citrate for 4 & 5; phosphate for 6 &7). Excess of dipyridamole was added to 0.25 ml of these solutions and were allowed to equilibrate for a minimum of 24 hours in a shaking waterbath at 25° C. (Preliminary experiments indicated that the equilibrium solubility was attained within 24 hr.). The solutions were centrifuged for 10 min. at 2500 rpm. 20 μl of the supernatant was carefully sampled using a 100 μl gas-tight Hamilton Syringe (Hamilton, NV), diluted with mobile phase and analyzed by HPLC. The solubility data was then used to determine the binding constant using the method of Higuchi and Connors for $A_L$-type phase behavior.

Physical Mixture Preparation:

Dipyridamole (SIGMA, MO), $(SBE)_7$-β-CD and citric acid (SIGMA, MO) (1:9:3 molar ratio) were physically mixed and ground manually using a mortar and pastel. The ground physical mixture was then sieved through a 200 mesh (75 μm) screen. This process was repeated twice. This mixture was always stored in a desiccator when not used.

Dissolution Die Description and Tablet Preparation:

The dissolution die consists of a cylindrical stainless steel center-piece, a stainless steel platform, a stainless steel top cover, two Teflon sheets (top and bottom) and Teflon inserts. The cylindrical center-piece has a hole (radius=7.5 mm) at the center in which the tablet is compressed. Both, the stainless steel top cover and top Teflon sheet have holes of same radius at the center. The center-piece was inverted and screwed onto the platform. Approximately, 120 mg of physical mixture containing drug, $(SBE)_7$-β-CD and citric acid was poured into the cylindrical hole and a punch was firmly placed in it. The tablet core was compressed with a force of one ton for one minute using Carver press (Fred Carver Inc., NJ). The punch was carefully removed from the center-piece by using a reverse hammer.

Film Coatings

Polymeric Solutions Preparation

Eudragit coatings were made by dissolving 5% (w/w) of Eudragit R or S (Huls America, NJ), 5% of urea (SIGMA, MO) or polyethylene glycol (PEG 3350, SIGMA, MO) and 0.75% of triethyl Citrate (TEC, SIGMA, MO) in 89.25% ethanol. This was carried out until a clear solution was obtained. Cellulose acetate (CA-320S, Eastman Chemical Co., TN) and hydroxypropylmethyl cellulose phthalate (HPMCP, Eastman Chemical Co., TN) polymeric solutions were made by dissolving 5% of polymers and 1% of TEC in 94% of solvent containing equal amounts of methylene chloride and methanol. The ratio of CA to HPMCP was varied from 50:50 to 75:25 but the total amount of polymer was always maintained at 5%. The dissolution was carried out until clear solutions were obtained.

Tablet Coating

This coating solution was then air sprayed directly on the tablet surface under constant air flow (approx. 70° C.). The coated tablets were dried additionally for a period of 15 minutes under the same air flow. The tablets were additionally dried for a period of 12–16 hr. at room temperature. The thickness of the membrane was assumed to be the difference of thickness of the tablet after and before coating. The thickness measurements were carried out using a Screw-gauge micrometer.

In vitro Release Studies

The release studies for tablets coated with Eudragit L and CA:HPMCP were conducted by placing the dissolution die in a USP dissolution apparatus II (Vanderkamp 600, VanKel Industries Inc.) containing 450 ml of HCl (pH 1.5, 37 C. and 100 r.p.m.). After 2 hr., the die was carefully removed and placed in 450 ml phosphate buffer (pH 1.5, 37° C. and 100 r.p.m.) and the dissolution experiment was continued. 1.5 ml samples were collected periodically and equal amounts of dissolution medium was returned to the dissolution vessel. For the CA:HPMCP coated tablet, 100% release was determined by removing the membrane from the die and allowing the drug dissolution to be complete. The release experiments for tablets coated with Eudragit S were conducted similarly in 450 ml of HCl for the first 2 hours, then placed in a phosphate buffer (pH 6.4) for additional 5 hr. and then placed in a phosphate buffer (pH 7.2). The release conditions and procedures were as described above.

0.5 ml of the sample was diluted by half in the mobile phase and the diluted samples were then analyzed using HPLC assay to determine drug concentrations as described in a later section. The rest of the sample was filtered through PVDF membrane (Fischer Scientific, NJ) and drug-free samples were then analyzed for $(SBE)_7$-β-CD by using the fluorimetric assay described below.

EXAMPLE 3

Methylprednisolone—$(SBE)_7$-β-CD

Sustained Release Formulation

Phase Solubility Studies

Excess amounts of methylprednisolone (MP) were added to 0.25 ml of $(SBE)_7$-β-CD solutions ranging from 0.0 to 0.2 mol/l. The dispersions were allowed to equilibrate for a minimum of 24 hours in a shaking waterbath (100 spm, 25° C.). The dispersions were centrifuged 10 min. at 2500 rpm, 20 μl of the supernatant were sampled with a gas-tight 100 μl syringe (Hamilton Co., NV), diluted with mobile phase and analysed by HPLC for the methylprednisolone concentration in solution. The methylprednisolone-$(SBE)_7$-β-CD binding constant $K_{1:1}$ was then determined by the method of Higuchi and Connors for an Type $A_L$ diagram.

Tablet Core Preparation

The tablet core was prepared with a 1/7 molar ratio of methylprednisolone/$(SBE)_7$-β-CD. This ratio was calculated using the previously determined binding constant in order to have sufficient $(SBE)_7$-β-CD in the tablet core to solubilize all the methylprednisolone present. Tablet cores with 1/3 and 1/10 ratios were also prepared to study the influence of the methylprednisolone/$(SBE)_7$-β-CD ratio on the release (cf. results 4). The tablet core consisted of either the methylprednisolone-$(SBE)_7$-β-CD complex or the physical mixture of the two compounds. The complex was prepared by freeze-drying a methylprednisolone-$(SBE)_7$-β-CD solution (5–15% in $(SBE)_7$-β-CD). Non $(SBE)_7$-β-CD containing tablets were also prepared. They consisted of a 1/7 ratio of methylprednisolone to a 50:50 (w/w) mixture of fructose and lactose (Fischer Scientific, NJ). The mixtures were ground in a mortar and sieved through a 200 mesh (75 μm) screen under low humidity conditions. The mixtures were stored in a dessicator when not used. Tablets of around 150 mg were compressed into the dissolution die using a Carver Laboratory Press (Fred S. Carver Inc., NJ) at 1 ton during 1 min.

Semi-permeable membrane preparation

The coating formulation was prepared by mixing 4.5% of ethylcellulose (Ethocel Standard 10 Premium, Dow Chemicals, MI) with an equivalent amount of poly(ethylene glycol) 3350 (PEG 3350, Sigma, MO). 0.9% of PEG 400 (Sigma, MO) and 90.1% of absolute ethanol were added to the mixture. The dispersion was shaken and sonicated until complete dissolution of the solid components. The coating solution was air sprayed (Airbrush, Paasche) on a Teflon surface under constant air flow (40° C.). At the end of the spraying, the membranes were dryed under the 40° C. air flow for 5 min. They were then left at room temperature during 24 hours. The membranes were peeled off the Teflon surface, checked for cracks and flaws under a light microscope (×70) and their thickness was measured using a micrometer (Ames, MA). The membranes were then secured on the dissolution die containing the tablet, with the face which was sprayed on the Teflon in contact with the tablet surface.

In vitro Release Studies

The release studies were realized by placing the dissolution die in a USP dissolution apparatus II (Vanderkamp 600, VanKel Industries Inc.) containing 350 ml of water at 37° C., 100 rpm. Samples were collected at various time points. The 100% release was determined by removing the membrane from the die and allowing the drug dissolution to be complete. The samples were analysed by HPLC and fluorimetric assays for methylprednisolone and $(SBE)_7$-$\beta$-CD concentrations respectively.

Methylprednisolone HPLC detection

Methylprednisolone was detected using a 15 cm ODS Hypersil column followed by UV detection at 254 nm (LC-10AT, Shimadzu scientific Instruments, Inc., Japan). The mobile phase was composed of 30% acetonitrile and 70% of pH 4.7 acetate buffer.

$(SBE)_7$-$\beta$-CD fluorimetric detection $(SBE)_7$-$\beta$-CD were detected by adding 0.2 ml of a 1E-3 mol/l solution of 2,6-toluidino-naphtalene-sulfonate to 0.8 ml of the sample. The solution was excited at 325 nm and the emitted fluorescence detected at 455 nm (650-40 Fluorescence Spectrophotometer, Perkin-Elmer, CT).

EXAMPLE 4

Tablet Comprising $SBE_7$-$\beta CD$ and a Therapeutic Agent

Tablet dosage forms according to the invention can generally be prepared as follows. A therapeutic agent and $SBE_7$-$\beta CD$ are dry blended for about 10 min. The remaining ingredients are added and the mixture is dry blended for about 10 min. The tablets are then compressed to a hardness of about 8–10 Kg. The following formulations can be used to prepare the dosage forms of the invention.

Indomethacin formulation

| Ingredient | Amount (mg) |
| --- | --- |
| 1: indomethacin | 25 |
| 1: $SBE_7$-$\beta CD$ | 300 |
| 2: EMDEX | 155 |
| 2: polyox-0.4 M (poly(ethylene oxide)) | 20 |
| 2: sucrose | 55 |
| 3: PRUV (Sodium stearyl fumerate) | 20 |
| 3: corn starch | 25 |
| Total | 600 |

The above ingredients are used to make a 600 mg tablet core having a rapid release profile. The numbers beside the ingredients indicates the general order of addition. After each group of ingredients is added, the mixture is dry blended for 5–10 min. Thus, PRUV and cornstarch are added in separately (step 3) from other ingredients and an additional 5 min. dry blend step is added to the general procedure.

Dipyridamole formulation

| Ingredient | Amount (mg) |
| --- | --- |
| dipyridamole | 25 |
| 1: $SBE_7$-$\beta CD$ | 300 |
| 2: citric acid | 53 |
| 2: PEG 3350 | 25 |
| 2: dextrose | 125 |
| 2: Cabosil M5P | 2 |
| 3: PRUV | 15 |
| 3: Ac-Di-Sol | 10 |
| Total | 555 |

The above ingredients are used to make a 555 mg tablet core having a rapid release profile. The numbers beside the ingredients indicates the general order of addition. After each group of ingredients is added, the mixture is dry blended for 5–10 min. Thus, PRUV and Ac-Di-Sol are added in separately (step 3) from other ingredients and an additional 5 min. dry blend step is added to the general procedure.

Piroxicam formulation

| Ingredient | Amount (mg) |
| --- | --- |
| 1: Piroxicam | 10 |
| 1: $SBE_4$-$\beta CD$ | 27 |
| 2: sorbitol | 45 |
| 2. dextrose | 100 |
| 2: citric acid | 10 |
| 2: xylitol | 49 |
| 2: PEG 3350 | 10 |
| 3: magnesium stearate | 0.5 |
| 3: croscarmellose sodium | 5.5 |
| Total | 257 |

The above ingredients are used to make a 500 mg tablet core having a rapid release profile. The numbers beside the ingredients indicates the general order of addition. After each group of ingredients is added, the mixture is dry blended for 5–10 min. Thus, PRUV and croscarmellose sodium are added in separately (step 3) from other ingredients and an additional 5 min. dry blend step is added to the general procedure.

Diltiazem formulation

| Ingredient | Amount (mg) |
| --- | --- |
| 1: diltiazem | 10 |
| 1: $SBE_7$-$\beta CD$ | 270 |
| 2: citric acid | 19 |
| 2: PEG 6000 | 5 |
| 2: dextrose | 249 |
| 2: sorbitol | 40 |
| 3: PRUV | 5 |
| 3: sodium starch glycolate | 2 |
| Total | 600 |

The above ingredients are used to make a 600 mg tablet having a rapid release profile. The numbers beside the ingredients indicates the general order of addition. After each group of ingredients is added, the mixture is dry blended for 5–10 min. Thus, PRUV and sodium starch glycolate are added in separately (step 3) from other ingredients and an additional 5 min. dry blend step is added to the general procedure.

Warfarin formulation

| Ingredient | Amount (mg) |
| --- | --- |
| 1: warfarin | 2 |
| 1: SBE$_7$-βCD | 150 |
| 2: EMDEX | 126 |
| 2: NaHCO$_3$ | 20 |
| 2: sodium lauryl sulfate | 2.0 |
| 3: PRUV | 15 |
| Total | 315 |

The above ingredients are used to make a 315 mg tablet core having a rapid release profile. The numbers beside the ingredients indicates the general order of addition. After each group of ingredients is added, the mixture is dry blended for 5–10 min. Thus, PRUV is added in separately (step 3) from other ingredients and an additional 5 min. dry blend step is added to the general procedure.

Methylprednisolone formulation

| Ingredient | Amount (mg) |
| --- | --- |
| 1: MP | 10 |
| 1: SBE$_4$-γCD | 200 |
| 2: xylitol | 155 |
| 2: pregelatinized starch | 150 |
| 2: sucrose | 33 |
| 3: PRUV | 12 |
| Total | 560 |

The above ingredients are used to make a 560 mg tablet core having a rapid release profile. The numbers beside the ingredients indicates the general order of addition. After each group of ingredients is added, the mixture is dry blended for 5–10 min. Thus, PRUV is added in separately (step 3) from other ingredients and an additional 5 min. dry blend step is added to the general procedure.

Indomethacin minitablet-gelatin capsule formulation

| Ingredient | Amount (mg) |
| --- | --- |
| 1: indomethacin | 25 |
| 1: SBE$_7$-βCD | 300 |
| 2: EMDEX | 155 |
| 2: polyox-0.4 M (poly(ethylene oxide)) | 20 |
| 2: sucrose | 55 |
| 3: PRUV (Sodium stearyl fumerate) | 20 |
| 3: corn starch | 25 |
| Total | 600 |

The above ingredients are used to make a 600 mg hard gelatin capsule comprising 3×200 mg film coated mini-tablets according to the invention. The uncoated mini-tablet cores have rapid release profiles. The mini-tablets are made as follows. The numbers beside the ingredients indicates the general order of addition. After each group of ingredients is added, the mixture is dry blended for 5–10 min. Thus, PRUV and cornstarch are added in separately (step 3) from other ingredients and an additional 5 min. dry blend step is added to the general procedure. The mixture is then divided into three equal parts and each part compressed into a mini-tablet. Following coating of the table core with a film forming agent of the invention according to the example below, the coated mini-tablets are placed within a hard gelatin capsule.

It should be noted that in several of the above examples, binders such as EMDEX and polyox-0.4M can be replaced with release controlling agents such as HPMC, HPC, cellulose acetate butyrate, cellulose acetate propionate, cellulose propionate, carrageenan, cellulose acetate, cellulose nitrate, methylcellulose, hydroxyethyl cellulose, ethylcellulose, polyvinyl acetate, latex dispersions, acacia, tragacanth, guar gum, gelatin, and the like. Thus, uncoated tablet cores having a controlled or sustained release profile can be prepared and further coated with the film forming agents of the invention to provide a tablet formulation having a combination delayed and controlled or sustained release profile, i.e. upon reaching a predetermined part of the GI tract, the film of the tablet will become porous and permit the therapeutic agent to be released from the tablet core in a controlled or sustained release fashion. A sustained or controlled release tablet core will be suitable for tablet formulations comprising a very water soluble film forming agent, a very porous film, a large amount of osmotic or solubilizing agents and other such conditions.

Alternative methods for preparation of the tablet core include, for example, dry granulation, wet granulation and compression-grinding-recompression. Accordingly, the dry granulation method can comprise preformation of a tablet or slugs with all tablet ingredients excluding the SAE-CD, grinding of the preformed tablet or slug, admixture of the ground material with an SAE-CD, and recompression of the mixture to form the desired tablet formulation.

Indomethacin controlled or sustained release tablet core formulation

| Ingredient | Amount (mg) |
| --- | --- |
| 1: indomethacin | 25 |
| 1: SBE$_7$-βCD | 300 |
| 2: HPMC | 100 |
| 2: sucrose | 55 |
| 3: PRUV (Sodium stearyl fumerate) | 20 |
| 3: corn starch | 25 |
| Total | 525 |

The above ingredients are used to make a 525 mg tablet core having a controlled or sustained release profile. The numbers beside the ingredients indicates the general order of addition. After each group of ingredients is added, the mixture is dry blended for 5–10 min. Thus, PRUV and cornstarch are added in separately (step 3) from other ingredients and an additional 5 min. dry blend step is added to the general procedure.

EXAMPLE 5

Tablet Core Made from Granules Comprising

SBE$_7$-βCD and a Therapeutic Agent

Tablet dosage forms according to the invention can contain granules and be made by wet granulation generally as follows. The indicated percentages correspond to weight percentages based on the final formulation weight. This example is based upon a 10 mg dose of methylprednisolone (MP). The therapeutic agent (20%) and SBE$_7$-βCD (375) are dry blended. Lactose (40%) and dextrose (8%) are wet granulated with PVP aqueous suspension (4%) until a 2% weight increase is obtained to form the desired granules.

NaHCO3 (3.5%), PRUV (4.5%), SiO$_2$ (0.5%) and xylitol (2%) are dry blended with the granules and the final mixture compressed into tablets to a hardness of about 8–10 Kg.

EXAMPLE 6

Tablet Film Coatings

Tablet film coatings according to the invention can be made using the following ingredients and conditions. The film coatings can be aqueous and/or solvent, e.g. alcohol, based. Generally, the film forming agent is dissolved or suspended in about ½ the volume of the projected solution volume, and the other ingredients are added. The mixture is then brought to final volume by further addition of water or solvent as desired. The resulting solution or suspension is used according to Example 7 to coat the tablet cores prepared as described above. The film compositions detailed below are based upon a 100 ml final solution or suspension volume.

EUDRAGIT RS film formulation:

| Ingredient | Amount (g) |
| --- | --- |
| EUDRAGIT RS | 15 |
| triethyl citrate (TEC) | 3 |
| talc | 7.5 |
| HPMC | 1.5 |

The EUDRAGIT RS is obtained as a 30% wt. suspension from the manufacturer. EUDRAGIT RS (film forming agent) is dissolved in water (50 ml) while stirring and the TEC, talc and HPMC (pore former) are subsequently added. The final solution volume is brought to 100 ml by the addition of more water. Other pore formers and film forming agents can be used.

EUDRAGIT RL 100 film formulation:

| Ingredient | Amount (g) |
| --- | --- |
| EUDRAGIT RL 100 | 15 (dry weight) |
| TEC | 3 |
| talc | 7.5 |
| HPC | 1.5 |

The EUDRAGIT RL can be formulated in isopropanol (IPA). EUDRAGIT RL is dissolved in IPA (50 ml) while stirring and the TEC, talc and HPC are subsequently added. The final solution volume is brought to 100 ml by the addition of more IPA.

EUDRAGIT RS/EUDRAGIT RL film formulation:

| Ingredient | Amount (g) |
| --- | --- |
| EUDRAGIT RS | 13.5 |
| EUDRAGIT RL | 1.5 |
| TEC | 3 |
| talc | 7.5 |
| HPC | 1.5 |

The EUDRAGIT RL and EUDRAGIT RS are mixed in water (50 ml) while stirring and the TEC, talc and HPC are subsequently added. The final solution volume is brought to 100 ml by the addition of more water. The EUDRAGIT RL serves to improve the water permeability of the EURO-DRAGIT as film.

Ethylcellulose film formulation:

| Ingredient | Amount (g) |
| --- | --- |
| ethylcellulose | 15 (dry weight) |
| dibutyl sebacate | 4.5 |
| talc | 8.0 |
| HPMC E5 | 1.5 |

The ethylcellulose is dissolved in water (50 ml) while stirring and the dibutyl sebacate, talc and HPMC E5 are subsequently added. The final solution volume is brought to 100 ml by the addition of more water. This same procedure can be conducted using IPA in place of water and HPC (1.0 g) in place of the HPMC E5.

Cellulose acetate film formulation:

| Ingredient | Amount (g) |
| --- | --- |
| cellulose acetate | 12 |
| TEC | 5 |
| talc | 7.5 |
| lactose | 1.5 |

The cellulose acetate is dissolved in water (50 ml) while stirring and the TEC, talc and lactose are subsequently added. The final solution volume is brought to 100 ml by the addition of more water. When using this film formulation, it may be necessary to operate the Hi-Coater at 45° C. or higher.

EUDRAGIT RS and EUDRAGIT L 100 film formulation:

| Ingredient | Amount (g) |
| --- | --- |
| EUDRAGIT RS | 15 |
| micronized EUDRAGIT L 100 | 1 |
| triethyl citrate (TEC) | 3 |
| talc | 7.5 |

The EUDRAGIT polymers are dissolved or suspended in water (50 ml) while stirring and the TEC and talc are subsequently added. The final solution volume is brought to 100 ml by the addition of more water. Other film forming agents such as cellulose acetate and HPMCP can be used in these combination film formulations.

EUDRAGIT L film formulation:

| Ingredient | Amount (g) |
| --- | --- |
| EUDRAGIT L | 15 |
| triethyl citrate (TEC) | 3 |
| talc | 7.5 |

The EUDRAGIT L is dissolved or suspended in water (50 ml) while stirring and the TEC and talc are subsequently added. The final solution volume is brought to 100 ml by the addition of more water. This film can be used to provide an enteric release tablet formulation and can be used to coat tablets already coated with other film coatings of the invention. The resulting tablet formulation will provide a formulation having a delayed controlled or sustained release of a therapeutic agent from the tablet core.

EXAMPLE 7

Coating of Tablet Core with Film Forming Agents

A film coated tablet formulation can be made generally as follows. It is contemplated that other equivalent conditions and equipment, as are known to the skilled artisan, can be used in the preparation of the present formulations without undue experimentation.

A Vector Hi-Coater (perforated pan tablet coater) is used under the following conditions:
inlet temperature 65°–75° C.
outlet temperature: 30°–35° C.
spray rate: 2–3 g/min
tablet load: 300 g
rotation speed: 20 rpm.

Following preparation of a solution or suspension containing the film forming agent and other ingredients (according to Example 6), tablet cores are placed inside the Hi-Coater and the film coating done until an about 100–125 μm thick film is formed. The coated tablets are dried at about 40° C. overnight. The tablet thickness and film composition can be varied as desired. The present method can be used on aqueous or solvent based film coating compositions.

The above is a detailed description of particular embodiments of the invention. Those with skill in the art should, in light of the present disclosure, appreciate that obvious modifications of the embodiments disclosed herein can be made without departing from the spirit and scope of the invention. All of the embodiments disclosed and claimed herein can be made and executed without undue experimentation in light of the present disclosure. The full scope of the invention is set out in the claims that follow and their equivalents. Accordingly, the claims and specification should not be construed to unduly narrow the full scope of protection to which the present invention is entitled.

REFERENCES

The following references, to the extent they provide exemplary procedural or other details supplementary to those set forth herein, are specifically incorporated herein by reference.

1. Pharmaceutical Dosage Forms-Tablets vol. 1, 2nd edition, Herbert A. Lieberman, ed. pp. 372–376.
2. U.S. Pat. No. 3,426,011 Parmerter et al.
3. U.S. Pat. No. 3,816,393 Hayashi et al.
4. U.S. Pat. No. 4,497,803 Harada et al.
5. U.S. Pat. No. 4,535,152 Szejtli et al.
6. U.S. Pat. No. 4,555,504 Jones
7. U.S. Pat. No. 4,582,900 Brandt et al.
8. U.S. Pat. No. 4,596,795 Pitha
9. U.S. Pat. No. 4,638,058 Brandt et al.
10. U.S. Pat. No. 4,727,064 Pitha
11. U.S. Pat. No. 4,746,734 Tsuchiyama et al.
12. U.S. Pat. No. 4,764,604 Mueller
13. U.S. Pat. No. 4,774,329 Friedman
14. U.S. Pat. No. 4,808,232 Beesley
15. U.S. Pat. No. 4,869,904 Uekama et al.
16. B. W. Mueller et al., Proceedings of the Fourth International Symposium on Cyclodextrins, (1988) pp. 369–382, "Cyclodextrin Derivatives for Solubilization, Stabilization, and Absorption of Drugs."
17. Josef Pitha, Third International Symposium on Recent Advances in Drug Delivery Systems, (1987), pp. 1–12, "Amorphous Water Soluble Derivatives of Cyclodextrins: From Test Tube to Patient."
18. U.S. Pat. No. 5,134,127 Stella et al.
19. M. E. Brewster et al., J. Pharm. Sci. (1988), 77(11), 981–985; "Improved delivery through biological membranes. XXXL: Solubilization and stabilization of an estradiol chemical delivery system by modified $SBE_7\beta$-CD -cyclodextrins."
20. N. Muranushi et al., Nippon Yakurigaku Zasahi (Japan) (1988), 91(6), 377–383; "Studies on benexate.CD: effect of inclusion compound formation on the anti-ulcer activity of benexate, the effective ingredient in benexate.CD."
21. J. J. Torres-Labandeira et al., STP Pharma. Sci. (1994), 4(3), 235–239; "Biopharmaceutical stability of the glibornuride/β-cyclodextrin inclusion complex after one year of storage."
22. D. Peri et al., Drug Dev. Ind. Pharm. (U.S.A) (1994), 20(4), 1401–1410; "Inclusion complexes of tolnaftate with β-cyclodextrin and hydroxypropyl b-cyclodextrin."
23. F. J. Otero-Espinar, et al., Int. J. Pharm. (Netherlands) (1991), 75(1), 37–44; "Oral bioavailability of naproxen-β-cyclodextrin inclusion complex."
24. S.-Y. Lin et al., Int. J. Pharm. (Netherlands) (1989), 56(3), 249–259; "Solid particulates of drug-β-cyclodextrin inclusion complexes directly prepared by a spray-drying technique."
25. M. T. Esclusa-Diaz et al., Int J. Pharm. (Amsterdam) (1996), 142(2), 183–187; "Preparation and evaluation of ketoconazole-β-cyclodextrin multi-component complexes."
26. U.S. Pat. No. 5,134,127 Stella, et al.

What is claimed is:

1. A pharmaceutical composition comprising a pharmaceutically acceptable carrier and a physical mixture of a sulfoalkyl ether-cyclodextrin derivative and a therapeutically effective amount of therapeutic agent wherein a major portion of the therapeutic agent is not complexed to the sulfoalkyl ether-cyclodextrin derivative.

2. The pharmaceutical composition of claim 1 wherein the sulfoalkyl ether-cyclodextrin derivative is a compound or mixture of compounds of the formula (I):

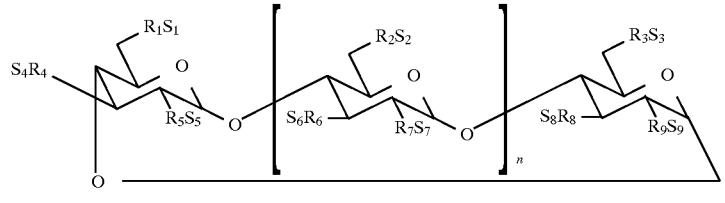

Formula (I)

wherein:
n is 4, 5 or 6;
$R_1$, $R_2$, $R_3$, $R_4$, $R_5$, $R_6$, $R_7$, $R_8$ and $R_9$ are each, independently, —O— or —O—(C2–C6 alkylene)—$SO_3$—, wherein at least one of $R_1$ and $R_2$ is independently —O—(C2–C6 alkylene)—$SO_3$—; and
$S_1$, $S_2$, $S_3$, $S_4$, $S_5$, $S_6$, $S_7$, $S_8$ and $S_9$ are each, independently, a pharmaceutically acceptable cation, wherein a major portion of the therapeutic agent is uncomplexed.

3. The pharmaceutical composition of claim 2 wherein:

at least one of $R_1$ and $R_2$ is —O—$(CH_2)_m$—$SO_3$—; and m is 2, 3, 4, 5 or 6.

4. The pharmaceutical composition of claim 3 wherein:

$S_1$, $S_2$, $S_3$, $S_4$, $S_5$, $S_6$, $S_7$, $S_8$ and $S_9$ are independently selected from the group consisting of:
alkaline metal cation, alkaline earth metal cation, quaternary ammonium cation, tertiary ammonium cation, and secondary ammonium cation.

5. The pharmaceutical composition of claim 1 wherein more than 50% of the therapeutic agent is uncomplexed.

6. The pharmaceutical composition of claim 3 wherein more than 75% of the therapeutic agent is uncomplexed.

7. The pharmaceutical composition of claim 4 wherein more than 95% of the therapeutic agent is uncomplexed.

8. A process for the preparation of a sulfoalkyl ether-cyclodextrin containing pharmaceutical dosage form comprising the steps of:

forming a solid core comprising a physical mixture of a sulfoalkyl ether-cyclodextrin derivative, a pharmaceutical carrier and an effective amount of a therapeutic agent, a major portion of which is not complexed to the sulfoalkyl ether-cyclodextrin derivative; and coating said solid core with a film coating comprising a film forming agent and a pore forming agent to provide a pharmaceutically acceptable solid dosage form.

9. The process for the preparation of a sulfoalkyl ether-cyclodextrin-containing solid dosage form according to claim 8, wherein the sulfoalkyl ether-cyclodextrin derivative is a compound of the formula (I):

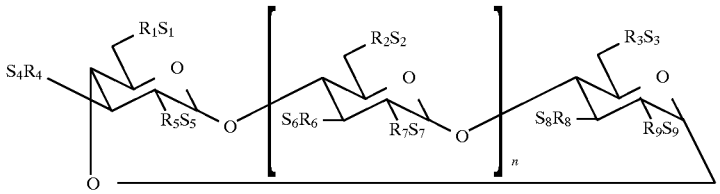

Formula (I)

wherein:

n is 4, 5 or 6;

$R_1$, $R_2$, $R_3$, $R_4$, $R_5$, $R_6$, $R_7$, $R_8$ and $R_9$ are each, independently, —O— or —O—(C2–C6 alkylene)—$SO_3$—, wherein at least one of $R_1$ and $R_2$ is independently —O—(C2–C6 alkylene)—$SO_3$—; and $S_1$, $S_2$, $S_3$, $S_4$, $S_5$, $S_6$, $S_7$, $S_8$ and $S_9$ are each, independently, a pharmaceutically acceptable cation, wherein a major portion of the therapeutic agent is uncomplexed.

10. The method of claim 9 wherein the sulfoalkyl ether-cyclodextrin derivative of the formula (I) is defined as follows:

n=4, 5 or 6;

$R_1$, $R_2$, $R_3$, $R_4$, $R_5$, $R_6$, $R_7$, $R_8$ and $R_9$ are each, independently, —O— or —O—(C2–C6 alkylene)—$SO_3$—, and at least one of $R^1$ and $R^2$ is, independently, —O—(C2–C6 alkylene)—$SO_3$—; and $S_1$, $S_2$, $S_3$, $S_4$, $S_5$, $S_6$, $S_7$, $S_8$ and $S_9$ are each, independently, a pharmaceutically acceptable cation.

11. The method of claim 9 wherein the sulfoalkyl ether-cyclodextrinderivative of the formula (I) is defined as follows:

$R_1$, $R_2$ and $R_3$ are each, independently, —O—(C2–C6 alkylene)—$SO_3$.

12. The method of claim 9 wherein the sulfoalkyl ether cyclodextrin derivative of the formula (I) is defined as follows:

at least one of $R_4$, $R_6$ and $R_8$ is independently, —O—(C2–C6 alkylene)—$SO_3$; and $R_5$, $R_7$ and $R_9$ are all —O—.

13. The method of claim 8 wherein the sulfoalkyl ether cyclodextrin derivative of the formula (I) is defined as follows:

$R_4$, $R_6$ and $R_8$ are each independently a —O—(C2–C6 alkylene)—$SO_3$— group.

14. A solid pharmaceutical formulation comprising a film coating and a solid core, wherein the film coating comprises a film forming agent and a pore forming agent, and the solid core comprises a pharmaceutically acceptable carrier and a physical mixture of a therapeutically effective amount of a therapeutic agent and a sulfoalkyl ether-cyclodextrin (SAE-CD), wherein a major portion of the therapeutic agent is not complexed to the SAE-CD.

15. The solid pharmaceutical formulation according to claim 14, wherein said film forming agent is selected from the group consisting of: cellulose acetate, ethylcellulose, methylcellulose, wax, methacrylate polymers, cellulose acetate phthalaate, hdroxypropyl methylcellulose phthalate, hydroxypropyl methylcellulose acetate succinate, cellulose acetate butyrate, cellulose acetate propionate, cellulose propionate, hydroxypropyl methylcellulose, carrageenan, cellulose nitrate, hydroxyethyl cellulose, poly(vinyl acetate), acacia, tragacanth, guar gum, gelatin and combinations thereof.

16. The solid pharmaceutical formulation according to claim 14, wherein said pore forming agent aids in the formation of pores in said film coating when said formulation is exposed to water.

17. The solid pharmaceutical formulation according to claim 14, wherein said pore forming agent increases the water permeability of said film coating.

18. The solid pharmaceutical formulation according to claim 14, wherein said formulation is a tablet, mini-tablet, granule, pellet, powder or crystal.

19. The solid pharmaceutical formulation of claim 14, wherein said formulation exhibits a delayed, sustained or controlled release profile for said therapeutic agent and said sulfoalkyl ether-cyclodextrin.

20. The solid pharmaceutical formulation of claim 19, wherein said formulation exhibits substantially the same release profile for said therapeutic agent and said sulfoalkyl ether-cyclodextrin.

* * * * *